United States Patent
Warner et al.

(10) Patent No.: US 10,047,089 B2
(45) Date of Patent: Aug. 14, 2018

(54) DIHYDRO-6-AZAPHENALENE DERIVATIVES FOR THE TREATMENT OF CNS, ONCOLOGICAL DISEASES AND RELATED DISORDERS

(71) Applicant: Collaborative Medicinal Development, LLC, Sausalito, CA (US)

(72) Inventors: John C. Warner, Wilmington, MA (US); Jeffery Allen Gladding, Burlington, MA (US); Srinivasa R. Cheruku, Lexington, MA (US); Dieu Nguyen, Wilmington, MA (US); Jean R. Loebelenz, Essex, MA (US); James J. Norman, Tewksbury, MA (US); Sambaiah Thota, Wilmington, MA (US); John W. Lee, Wilmington, MA (US); Craig Rosenfeld, Dallas, TX (US)

(73) Assignee: Collaborative Medicinal Development, LLC, Sausalito, CA (US)

( * ) Notice: Subject to any disclaimer, the term of this patent is extended or adjusted under 35 U.S.C. 154(b) by 610 days.

(21) Appl. No.: 14/040,393

(22) Filed: Sep. 27, 2013

(65) Prior Publication Data

US 2014/0094487 A1    Apr. 3, 2014

Related U.S. Application Data

(60) Provisional application No. 61/707,444, filed on Sep. 28, 2012.

(51) Int. Cl.
*C07D 471/06*    (2006.01)
(52) U.S. Cl.
CPC .................. *C07D 471/06* (2013.01)
(58) Field of Classification Search
CPC .................................................. C07D 471/06
USPC ........................................... 514/292; 546/81
See application file for complete search history.

(56) References Cited

U.S. PATENT DOCUMENTS

| | | |
|---|---|---|
| 6,380,193 B1 | 4/2002 | Li et al. |
| 6,417,178 B1 | 7/2002 | Klunk et al. |
| 7,619,091 B2 | 11/2009 | Barnham et al. |
| 2008/0161353 A1 | 7/2008 | Barnham et al. |
| 2010/0314556 A1 | 12/2010 | Hamel et al. |
| 2015/0094334 A1 | 4/2015 | Barnham et al. |

FOREIGN PATENT DOCUMENTS

| | | |
|---|---|---|
| CN | 102603695 A | 7/2012 |
| JP | 63-22078 A | 1/1988 |
| JP | 03-232858 A | 10/1991 |
| JP | 2002-515490 A | 5/2002 |
| JP | 2009-507861 A | 2/2009 |

OTHER PUBLICATIONS

Brana et al., "Synthesis, Biological Activity, and Quantitative Structure-Activity Relationship Study of Azanaphthalimide and Arylnaphthalimide Derivatives", J. Med. Chem. 2004, vol. 47, pp. 2236-2242.
Clayton, J., et al., "Cyclization of Lithiated Pyridine and Quinoline Carboxamides: Synthesis of Partially Saturated Pyrrolopyridines and Spirocyclic β-Lactams," Organic Lett. 2005;7(17):3673-3676.
Extended European Search Report for European Patent App. No. 13842204.3 (dated Mar. 21, 2016).
Zee-Cheng, R. K. Y., et al., "N-(Aminoalkyl)imide Antineoplastic Agents, Synthesis and Biological Activity," J. Med. Chem. 1985;28:1216-1222.
Official Action from Japanese Patent App. No. 2015-534773 dated Jul. 7, 2017.

*Primary Examiner* — Rita J Desai
(74) *Attorney, Agent, or Firm* — Cermak Nakajima & McGowan LLP; Malcolm K. McGowan

(57) ABSTRACT

In one embodiment, the present application discloses 2-aza-, 2-oxa- and 2-thia-2,3-dihydro-6-azaphenalene compounds and compositions, and methods for treating a neurological disease in a patient in need thereof using the compounds and compositions as disclosed herein.

20 Claims, 7 Drawing Sheets

Figure 1: Measurement of aggregation prevention by added zinc and disaggregation of zinc induced aggregates by AC047 in a bisANS assay.
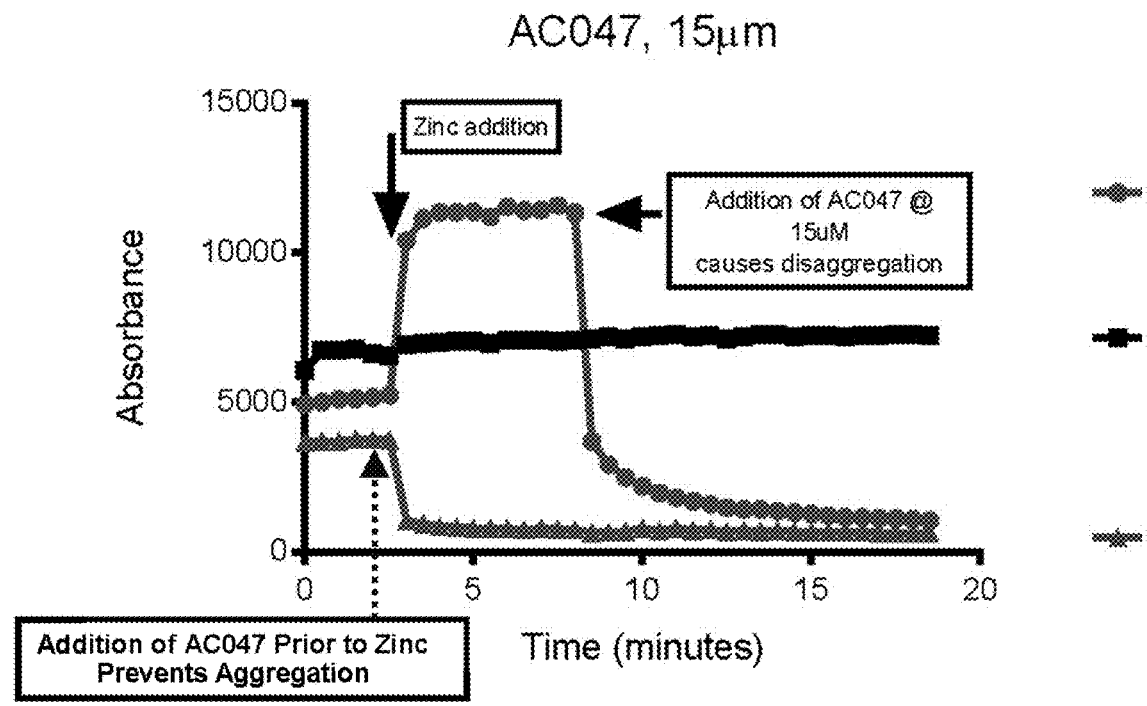

Figure 2: Prevention of Aß aggregation at compound concentrations ranging from 0.11 to 7.5 µM.
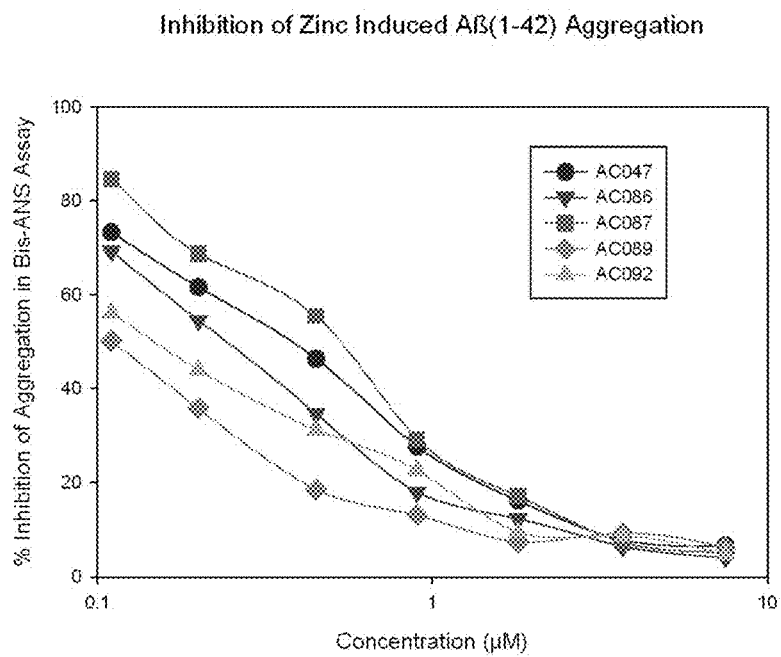

Figure 3: Elimination of Aβ aggregates at compound concentrations ranging from 0.11 to 7.5 µM.
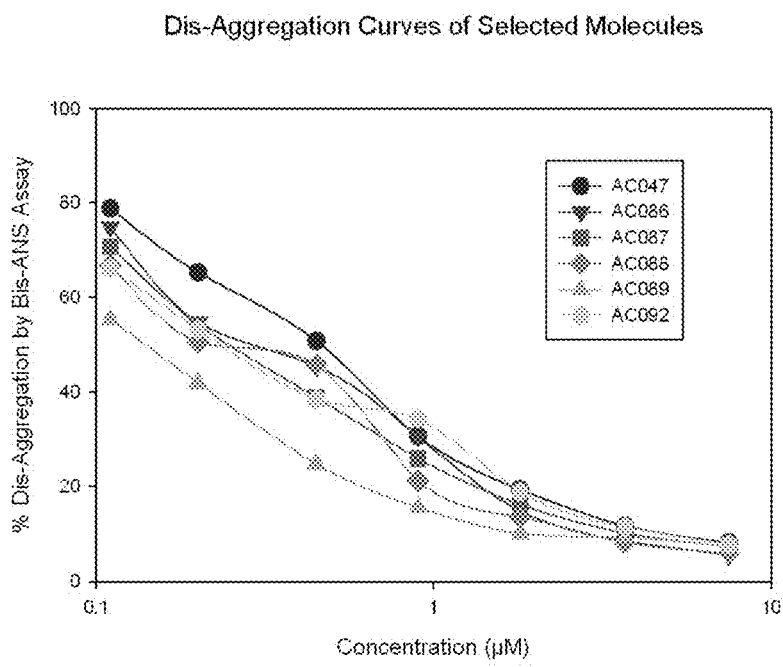

Figure 4: Calculated EC$_{50}$ concentrations for aggregation prevention by new compounds.
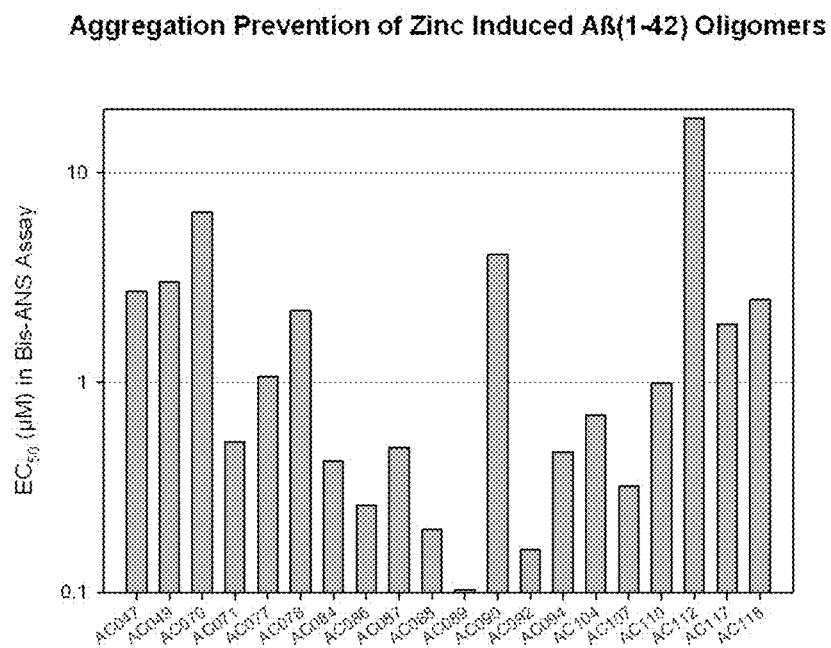

Figure 5: Calculated EC$_{50}$ concentrations for aggregation elimination by new compounds.
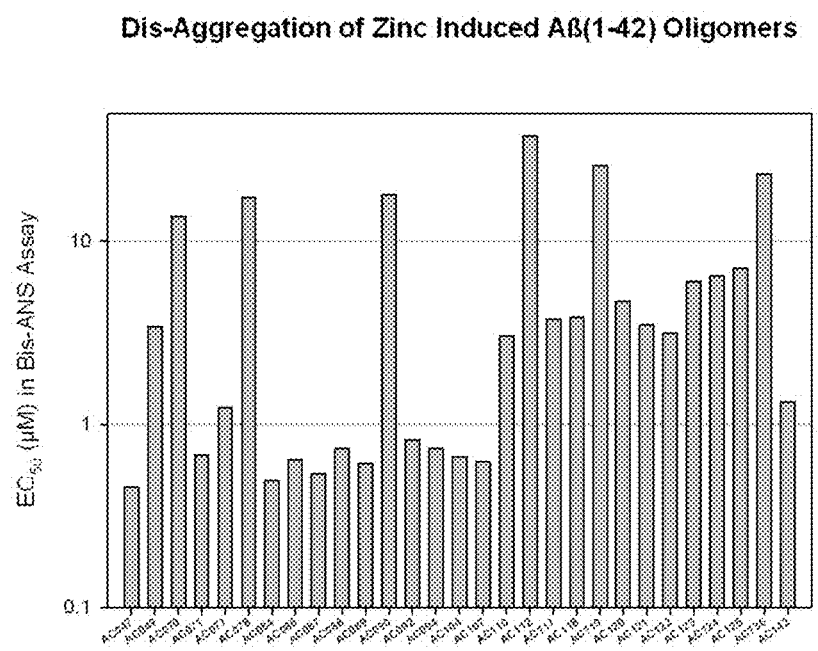

Figure 6: Copper Ionophore Assay on M17 Cells; Assays performed with 10 μM CuSO$_4$ + 10 μM Ionophore.
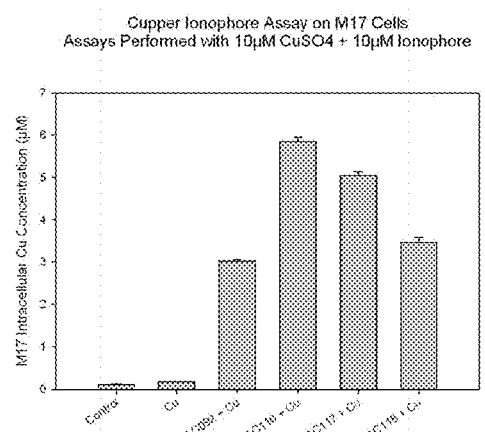

Figure 7: Inhibition of ThT Assay by 5 μM Test Molecule
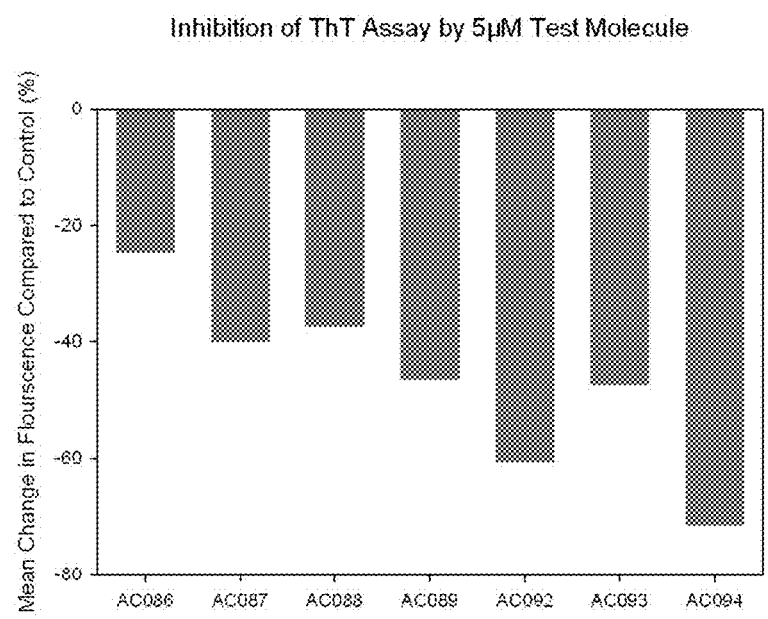

DIHYDRO-6-AZAPHENALENE DERIVATIVES FOR THE TREATMENT OF CNS, ONCOLOGICAL DISEASES AND RELATED DISORDERS

RELATED APPLICATION

This application claims the benefit of U.S. Provisional Application No. 61/707,444 filed Sep. 28, 2012, which is incorporated herein by reference.

BACKGROUND OF THE INVENTION

Presently, there are no known prevention or cure for neurodegenerative diseases or disorders such as Alzheimer's disease (AD), Parkinson's disease (PD) and prion diseases (PrDs). It has been demonstrated that an aberrant protein has a propensity to misfold in the presence of certain concentrations of metal ions. The present application discloses compounds, compositions and methods for the treatment of such diseases or disorders.

SUMMARY OF THE INVENTION

There is a continuing need for the synthesis and development of novel and effective compounds that are selective neuroactive agents for the treatment of diseases of the central nervous system (CNS) and for oncological diseases. In one aspect, the selective neuroactive agents are ion chelators, including copper, zinc and iron etc. . . . The following embodiments, aspects and variations thereof are exemplary and illustrative are not intended to be limiting in scope.

In one embodiment, the present application discloses novel 2-aza-, 2-oxa- and 2-thia-2,3-dihydro-6-azaphenalene derivatives with optimized protein aggregation and disaggregation properties for use in CNS and oncological diseases. In one aspect, the 2,3-dihydro-6-azaphenalene derivatives are metal active agents.

In one embodiment, the present application provides a compound of the formula I:

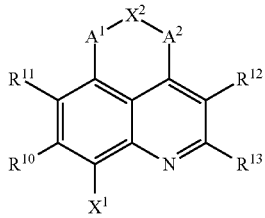

I wherein:
$X^1$ is —$OR^1$ or —$NR^1R^2$;
$X^2$ is selected from the group consisting of —$NR^3$—, —O— and —$S(O)_{1-2}$—;
$A^1$ is selected from the group consisting of —$C(R^4R^5)$—, —C(O)—, —C(S)— and —$C(NR^6)$—;
$A^2$ is selected from the group consisting of —$C(R^7R^8)$—, —C(O)—, —C(S)— and —$C(NR^9)$—;
$R^1$ and $R^2$ are each independently H, substituted or unsubstituted $C_1$-$C_6$ alkyl, X—$C_1$-$C_6$ alkyl, substituted or unsubstituted $C_{5-10}$ aryl, substituted or unsubstituted —$C_{1-6}$ alkyl-$C_{6-10}$ aryl, substituted or unsubstituted $C_{1-6}$ alkylC(O)—, X—$C_{1-6}$ alkylC(O)—, substituted or unsubstituted $C_{1-6}$ alkylS(O)$_{1-2}$—, substituted or unsubstituted $C_{1-6}$ alkylNR'C(O)—, X—$C_{1-6}$ alkylNR'C(O)—, X—$C_{1-6}$ alkoxyC(NR")— and substituted or unsubstituted $C_{1-6}$ alkoxyC(NR")—;

R' and R" are each independently selected from the group consisting of H, substituted or unsubstituted $C_{1-6}$ alkyl and substituted and unsubstituted —$C_{1-6}$ alkyl-$C_{6-10}$ aryl;

$R^3$ is H or selected from the group consisting of substituted or unsubstituted $C_{1-6}$ alkyl, substituted or unsubstituted $C_{5-10}$ aryl, substituted or unsubstituted —$C_{1-6}$ alkyl-$C_{6-10}$ aryl, substituted or unsubstituted —$C_{1-6}$ alkyl-$C_{5-10}$ heteroaryl, substituted or unsubstituted $C_{1-6}$ alkylC(O)—, substituted or unsubstituted $C_{1-6}$ alkyl-$S(O)_{1-2}$—, substituted or unsubstituted $C_{1-6}$ alkylNHC(O)— and substituted or unsubstituted $C_{1-6}$ alkoxyC(NR')—;

$R^4$, $R^5$, $R^6$, $R^7$, $R^8$ and $R^9$ are each independently H or selected from the group consisting of substituted or unsubstituted $C_{1-6}$ alkyl, substituted or unsubstituted $C_{1-6}$ alkylC(O)—, substituted or unsubstituted $C_{1-6}$ alkoxyC(O)—, substituted or unsubstituted —$C_{1-6}$ alkyl-$C_{6-10}$ aryl and substituted or unsubstituted $C_{5-10}$ aryl;

$R^{10}$, $R^{11}$ and $R^{12}$ are each independently H or selected from the group consisting of substituted or unsubstituted $C_{1-6}$ alkyl, X—$C_{1-6}$ alkyl, X—$C_{1-6}$ alkylC(O)— and substituted or unsubstituted $C_{1-6}$ alkylC(O)—;

$R^{13}$ is H or is selected from the group consisting of X, halo, —OR', —CN, —SR', —NR'R", —$NO_2$, —$CO_2R'$, —$SO_3R'$, substituted or unsubstituted $C_{1-6}$ alkyl, $C_{1-6}$ alkyl-X, —$C_{1-6}$ alkyl-SH, substituted or unsubstituted $C_{1-6}$ alkoxy-, substituted or unsubstituted $C_{1-6}$ alkylC(O)—, X—$C_{1-6}$ alkylC(O)—, substituted or unsubstituted $C_{1-6}$ alkylC(S)—, X—$C_{1-6}$ alkylC(S)—, —$(CH_2)_n$—NH—$(CH_2)_m$—NR'R", $C_{1-6}$ alkylC(NR')—, X—$C_{1-6}$ alkylC(NR')—, X—$C_{1-6}$ alkylC(NOH)—, $C_{1-6}$ alkylC(NOH)—, —$(CH_2)_n$—C(NOH)—$C_{1-6}$ alkyl, $C_{5-10}$ aryl, —$C_{1-6}$ alkyl-$C_{6-10}$ aryl, —$C_{1-6}$ alkyl-$C_{3-10}$ heteroaryl and —$C_{3-10}$ heteroaryl;

each X is independently selected from the group consisting of $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O and $^{76}$Br;

m and n are each independently 1, 2 or 3; or a pharmaceutically acceptable salt thereof.

In one aspect of the above compound, $X^1$ is —OH. In another aspect of the above compounds, $X^2$ is $NR^3$, wherein $R^3$ is a substituted or unsubstituted $C_{1-6}$ alkyl- or a substituted or unsubstituted —$C_{1-6}$ alkyl-$C_{6-10}$ aryl. In one variation, the —$C_{6-10}$ aryl group of the —$C_{1-6}$ alkyl-$C_{6-10}$ aryl group is a phenyl, and the substitution on the phenyl group is ortho, meta or para substitution. In another aspect, the substitution is selected from fluoro, chloro, bromo or iodo. In one variation of the above, $R^3$ a substituted or unsubstituted $C_{1-6}$ alkyl- or a substituted or unsubstituted —$C_{1-6}$ alkyl-$C_{6-10}$ aryl where the substitution is selected from the group consisting of $^{131}$I, $^{124}$I, $^{125}$I, $^{123}$I, $^{18}$F, $^{19}$F, $^{75}$Br and $^{76}$Br.

In another aspect of the above, $A^1$ and $A^2$ are each independently —C(O)— or —$CH_2$—. In yet another aspect of the above, $R^{10}$, $R^{11}$, $R^{12}$ and $R^{13}$ are hydrogen. In a particular variation of the above, $R^3$ is H or selected from the group consisting of methyl, ethyl, propyl, allyl, propargyl and N-benzyl. In one aspect of the above, $R^3$ is $C_{1-6}$ alkyl-X, wherein X is selected from the group consisting of $^{131}$I, $^{124}$I, $^{125}$I, $^3$H, $^{123}$I, $^{18}$F, $^{19}$F, $^{75}$Br and $^{76}$Br. In another aspect of the above compound, X is $^{18}$F.

A compound of the formula II:

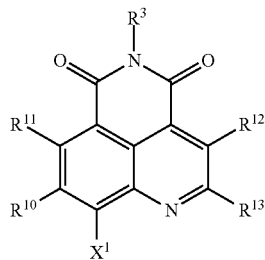

wherein:

$X^1$ is —$OR^1$ or —$NHR^2$;

$R^1$ and $R^2$ are each independently H, X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$ alkylC(O)—, substituted or unsubstituted $C_{1-6}$ alkylC(O)—, X—$C_{1-6}$ alkyl-S(O)$_{1-2}$—, substituted or unsubstituted $C_{1-6}$ alkyl-S(O)$_{1-2}$—, X—$C_{1-6}$ alkylNHC(O)—, substituted or unsubstituted $C_{1-6}$ alkyl-NHC(O)—, X—$C_{1-6}$ alkoxyC(NH)— and substituted or unsubstituted $C_{1-6}$ alkoxyC(NH)—;

$R^3$ is H or selected from the group consisting of X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$ alkylC(O)—, substituted or unsubstituted $C_{1-6}$ alkylC(O)—, X—$C_{1-6}$ alkylS(O)$_{1-2}$ substituted or unsubstituted $C_{1-6}$ alkylS(O)$_{1-2}$—, substituted or unsubstituted $C_{1-6}$ alkylNHC(O)—, X—$C_{1-6}$ alkoxyC(NH)— and substituted or unsubstituted $C_{1-6}$ alkoxyC(NH)—;

$R^{10}$, $R^{11}$ and $R^{12}$ are each independently H, X or selected from the group consisting of X—$C_{1-6}$ alkyl, substituted or unsubstituted $C_{1-6}$ alkyl, X—$C_{1-6}$ alkylC(O)— and substituted or unsubstituted $C_{1-6}$ alkylC(O)—;

$R^{13}$ is H or is selected from the group consisting of X, halo, —OR', —CN, —SR', —NR'R", —$NO_2$, —$CO_2R'$, —$SO_3R'$, substituted or unsubstituted $C_{1-6}$ alkyl, —$C_{1-6}$ alkyl-SH, substituted or unsubstituted $C_{1-6}$ alkoxy-, substituted or unsubstituted $C_{1-6}$ alkylC(O)—, substituted or unsubstituted $C_{1-6}$ alkylC(S)—, —$(CH_2)_n$—NH—$(CH_2)_m$—NR'R", $C_{1-6}$ alkylC(NR')—, $C_{1-6}$ alkylC(NOH)—, —$(CH_2)_n$—C(NOH)—$C_{1-6}$ alkyl, $C_{6-10}$ aryl, —$C_{1-6}$ alkyl-$C_{6-10}$ aryl, —$C_{1-6}$ alkyl-$C_{3-10}$ heteroaryl and —$C_{3-10}$ heteroaryl;

R' and R" are each independently selected from the group consisting of H, substituted or unsubstituted $C_{1-6}$ alkyl and substituted or unsubstituted —$C_{1-6}$ alkyl-$C_{6-10}$ aryl;

each X is independently selected from the group consisting of $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$ and $^{76}Br$;

m and n are each independently 1, 2 or 3; or a pharmaceutically acceptable salt thereof.

In one aspect of the above compound, $X^1$ is —OH and $R^{10}$, $R^{11}$, $R^{12}$ and $R^{13}$ are hydrogen. In another aspect, $R^3$ is selected from the group consisting of $C_{1-6}$ alkyl and substituted or unsubstituted —$C_{1-6}$ alkyl-$C_{6-10}$ aryl. In another aspect of the above, $X^1$ is —OH; $R^{10}$, $R^{11}$ and $R^{12}$ are hydrogen; $R^3$ is —$C_{1-6}$ alkyl-$C_{6-10}$ aryl or —$C_{1-6}$ alkyl-$C_{6-10}$ aryl-X, including -2-halo-benzyl (such as 2-fluoro-benzyl), 3-halo-benzyl (such as 3-fluoro-benzyl) or 4-halo-benzyl (such as 4-fluoro-benzyl); and $R^{13}$ is H or is selected from the group consisting of —OR', —SR', —NR'R", —$CO_2R'$, —$SO_3R'$, —$C_{1-6}$ alkyl-SH, substituted or unsubstituted $C_{1-6}$ alkoxy-, substituted or unsubstituted $C_{1-6}$ alkylC(O)—, substituted or unsubstituted $C_{1-6}$ alkylC(S)—, —$(CH_2)_n$—NH—$(CH_2)_m$—NR'R", $C_{1-6}$ alkylC(NR')—, $C_{1-6}$ alkylC(NOH)—, —$(CH_2)_n$—C(NOH)—$C_{1-6}$ alkyl, —$C_{1-6}$ alkyl-$C_{3-10}$ heteroaryl and —$C_{3-10}$ heteroaryl. In another aspect of the above, $R^3$ is —$C_{1-6}$ alkyl-X, wherein X is selected from the group consisting of $^{131}I$, $^{124}I$, $^{125}I$, $^{3}H$, $^{123}I$, $^{18}F$, $^{19}F$, $^{75}Br$ and $^{76}Br$. In one variation of the above, X is $^{18}F$. In another variation, at least one of $R^{10}$, $R^{11}$, $R^{12}$ and $R^{13}$ is X.

In another embodiment, there is provided a compound of the formula III:

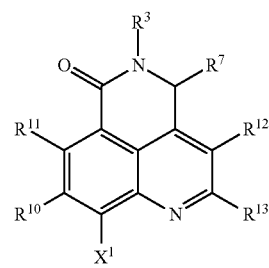

wherein:

$X^1$ is —$OR^1$ or $NHR^2$;

$R^1$ and $R^2$ are each independently H, X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$ alkylC(O)—, substituted or unsubstituted $C_{1-6}$ alkylC(O)—, X—$C_{1-6}$ alkyl-S(O)$_{1-2}$—, substituted or unsubstituted $C_{1-6}$ alkyl-S(O)$_{1-2}$—, X—$C_{1-6}$ alkylNHC(O)—, substituted or unsubstituted $C_{1-6}$ alkyl-NHC(O)— and substituted, X—$C_{1-6}$ alkoxyC(NH)—, or unsubstituted $C_{1-6}$ alkoxyC(NH)—;

$R^3$ is H or selected from the group consisting of X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$ alkylC(O)—, substituted or unsubstituted $C_{1-6}$ alkylC(O)—, X—$C_{1-6}$ alkylS(O)$_{1-2}$—, substituted or unsubstituted $C_{1-6}$ alkylS(O)$_{1-2}$—, X—$C_{1-6}$ alkylNHC(O)—, substituted or unsubstituted $C_{1-6}$ alkylNHC(O)—, X—$C_{1-6}$ alkoxyC(NH)— and substituted or unsubstituted $C_{1-6}$ alkoxyC(NH)—;

$R^7$ is H or is selected from the group consisting of substituted or unsubstituted $C_{1-6}$ alkyl, substituted or unsubstituted $C_{1-6}$ alkylC(O)—, substituted or unsubstituted $C_{1-6}$ alkoxyC(O)—, substituted or unsubstituted —$C_{1-6}$ alkyl-$C_{6-10}$ aryl and substituted or unsubstituted $C_{5-10}$ aryl;

$R^{10}$, $R^{11}$ and $R^{12}$ are each independently H, X or selected from the group consisting of substituted or unsubstituted $C_{1-6}$ alkyl and substituted or unsubstituted $C_{1-6}$ alkylC(O)—;

$R^{13}$ is H or is selected from the group consisting of X, halo, —OR', —CN, —SR', —NR'R", —$NO_2$, —$CO_2R'$, —$SO_3R'$, substituted or unsubstituted $C_{1-6}$ alkyl, —$C_{1-6}$ alkyl-SH, substituted or unsubstituted $C_{1-6}$ alkoxy-, substituted or unsubstituted $C_{1-6}$ alkylC(O)—, substituted or unsubstituted $C_{1-6}$ alkylC(S)—, —$(CH_2)_n$—NH—$(CH_2)_m$—NR'R", $C_{1-6}$ alkylC(NR')—, $C_{1-6}$ alkylC(NOH)—, —$(CH_2)_n$—C(NOH)—$C_{1-6}$ alkyl, $C_{6-10}$ aryl, —$C_{1-6}$ alkyl-$C_{6-10}$ aryl, —$C_{1-6}$ alkyl-$C_{3-10}$ heteroaryl and —$C_{3-10}$ heteroaryl;

R' and R" are each independently selected from the group consisting of H, substituted or unsubstituted $C_{1-6}$ alkyl and substituted or unsubstituted —$C_{1-6}$ alkyl-$C_{6-10}$ aryl;

each X is independently selected from the group consisting of $^{131}$I, $^{124}$I, $^{125}$I, $^{3}$H, $^{123}$I, $^{18}$F, $^{19}$F, $^{75}$Br and $^{76}$Br;

m and n are each independently 1, 2 or 3; or a pharmaceutically acceptable salt thereof.

In one aspect of the above compounds, when $R^7$ is phenyl and $X^1$ is —OH, then $R^3$ is not benzyl.

In one aspect of the above compound, $X^1$ is OH and $R^{10}$, $R^{11}$, $R^{12}$ and $R^{13}$ are hydrogen. In another aspect of the above, $R^3$ is selected from the group consisting of $C_{1-6}$ alkyl and —$C_{1-6}$ alkyl-$C_{6-10}$ aryl. In another aspect of the above compound, $X^1$ is OH; $R^{10}$, $R^{11}$ and $R^{12}$ are hydrogen; $R^3$ is —$C_{1-6}$ alkyl-$C_{6-10}$ aryl; and $R^{13}$ is H or is selected from the group consisting of —OR', —SR', —NR'R", —CO$_2$R', —SO$_3$R', —$C_{1-6}$ alkyl-SH, substituted or unsubstituted $C_{1-6}$ alkoxy-, substituted or unsubstituted $C_{1-6}$ alkylC(O)—, substituted or unsubstituted $C_{1-6}$ alkylC(S)—, —(CH$_2$)$_n$—NH—(CH$_2$)$_m$—NR'R", $C_{1-6}$ alkylC(NR')—, $C_{1-6}$ alkylC(NOH)—, —(CH$_2$)$_n$—C(NOH)—$C_{1-6}$ alkyl, —$C_{1-6}$ alkyl-$C_{3-10}$ heteroaryl and —$C_{3-10}$ heteroaryl. In another aspect, at least one of $R^{10}$, $R^{11}$, $R^{12}$ and $R^{13}$ is X.

As provided herein, when the above compound or composition comprises the substituent X, the compound or composition may be referred to as a probe or having a probe. In another aspect of the above compound of the formula I, II or III, the compound is labeled with an atom selected from the group consisting of $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O and $^{76}$Br.

In another aspect of the above compounds, the compounds include the pharmaceutically acceptable salt thereof, optionally in the form of a single stereoisomer or mixture of stereoisomers thereof. In another aspect of the application, there is provided a pharmaceutical composition comprising a therapeutically effective amount of any of the above compounds, and a pharmaceutically acceptable excipient.

In another embodiment, there is provided a method for treating an ocular disease in a patient in need thereof, comprising administering to the patient a therapeutically effective amount of the above compounds or compositions. In one aspect of the method, the ocular disease is selected from the group consisting of macular degeneration, retinitis pigmentosa, retinopathy, glaucoma and cataracts.

In another embodiment, there is provided a method for treating a neurological disease in a patient in need thereof comprising administering to the patient a therapeutically effective amount of the above compounds or compositions. In one aspect of the embodiment, the neurological disorder or disease is a neurodegenerative disease.

In another aspect of the above, the neurological disorder or disease is a neurodegenerative, neurodevelopmental or neuropsychiatric disorder. In another aspect of the above method, the neurodegenerative disorder or disease is selected from the group consisting of Alzheimer's disease (AD), amyotrophic lateral sclerosis (ALS), motor neuron disease, Parkinson's disease, Huntington Disease, prion disease, AIDS or HIV related dementia, cerebral ischemia, cerebrovascular disease, cerebral hemorrhage, Downs Syndrome, epilepsy, traumatic brain injury, chronic traumatic encephalopathy, traumatic spinal injury, Friedrich's Ataxia, frontotemporal dementia, hemorrhagic stroke, Neurodegeneration with Brain Iron Accumulation, Lewy Body Disease, ischemic stroke, multiple sclerosis, Pick's Disease, progressive supranuclear palsy, senile dementia, mild cognitive impairment, hereditary cerebral hemorrhage, traumatic ischemia attack, lead encephalopathy, subdural hematoma, radiation brain injury, Niemann-Pick Disease and neuronal ceroid lipofuscinoses (NCLs; Batten disease).

In another embodiment, there is provided a method for inhibiting protein aggregation in a patient comprising the administration of a therapeutically effective amount of the above compound or composition to the patient. In one aspect of the above method, the therapeutically effective amount is effective to treat a disease selected from the group consisting of Alzheimer's disease (AD), amyotrophic lateral sclerosis (ALS), motor neuron disease, Parkinson's disease, Huntington Disease and prion disease. In another aspect, the therapeutically effective amount is effective to treat a disease selected from the group consisting of AA amyloidosis, light chain amyloidosis, familial amyloid polyneuropathies, AA (Inflammatory) amyloidosis, amylin related amyloidosis, familial visceral amyloidosis, primary cutaneous amyloidosis, cerebral amyloid angiopathy, familial corneal amyloidosis and medullary carcinoma of the thyroid.

In another embodiment, there is provided a method for treating a metal ion associated disorder or disease in a patient in need thereof comprising administering to the patient a therapeutically effective amount of the above cited compound or composition. In one aspect of the method, the metal ion associated disorder or disease, such as a metal ion associated neurological disorder or disease, is selected from the group consisting of acrodermatitis enteropathica, Menkes Disease, cholelithiasis and nephrolithiasis.

In another embodiment, there is provided an in vivo method for detecting amyloid deposits in a patient comprising administering an effective amount of compound or composition of the above, comprising a probe to the patient having or suspected of having an amyloidosis-related disorder or disease and detecting the binding of the probe to at least one amyloid deposit in the patient.

Measurement of inhibition or reversal of protein aggregation may be carried out using such assays as Bis-ANS Fluorescence as described in, for example, W. T. Chen et al., *J. Biol. Chem*, 2011, 286 (11), 9646, or thioflavin T assay as disclosed herein.

In another embodiment, there is provided compounds and amyloid probes as a method for diagnosing a neurological disease or disorder, such as AD and other disorders or diseases as disclosed herein and quantifying the extent or progression of amyloid deposits or plaques by in vivo imaging of amyloid and/or amyloid deposits in the regions of the brain. In one aspect, the amyloid probe may be administered to a patient in amounts suitable for in vivo imaging of amyloid deposits. In another aspect, the amyloid probe may be used to detect and quantify amyloid deposits in various diseases or disorders, such as AD.

The application also discloses an in vivo or in vitro method for detecting in a patient, one or more amyloid deposits. In one aspect, the amyloid deposit may comprise one or more amyloid or amyloidogenic protein. In one aspect, the method comprises administering to a patient suffering from a disorder or disease associated with amyloidosis, a detectable quantity (effective amount) of a compound, amyloid probe or a composition as disclosed herein. An amyloid probe may comprise one or more substituent X as a label (radiolabel, tracer, marker or tag). An amyloid probe may comprise one or more radionuclides, radioisotopes or isotopes (labels). Examples of radiolabels include $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O and $^{76}$Br. The method also comprises detecting the binding of the compound or probe to an amyloid deposit (or plaque). An amyloid deposit may comprise amyloid or amyloidogenic proteins (or precursors, portions, fragments and peptides thereof, as disclosed herein). Examples of precursor and amyloidogenic proteins as well as amyloidosis-related diseases are generally described in International Publication No. WO 2007/035405, which is incorporated by reference herein.

In another embodiment, there is provided an in vivo method for detecting amyloid deposits in a patient comprising administering an effective amount of the above compound or composition comprising a probe to the patient having or suspected of having an amyloidosis-related disorder or disease and detecting the binding of the probe to at least one amyloid deposit in the patient. In one aspect of the method, the amyloid deposit is located in the brain of the patient. In another aspect, the patient has, is suspected of having or is at risk for an amyloidosis-related disorder or disease. In another aspect, the amyloidosis-related disorder or disease is AD and other disorder or diseases as disclosed herein. In another aspect of the method, the detection is by gamma imaging, magnetic resonance imaging, magnetic resonance spectroscopy or fluorescence spectroscopy. In another aspect of the method, the detection is by gamma imaging, magnetic resonance imaging, magnetic resonance spectroscopy or fluorescence spectroscopy. In another aspect of the method, the detection is by gamma imaging is PET or SPECT.

In one aspect of the method, the pharmaceutical composition comprising the substituent X, referred to herein as a probe or an amyloid probe, may also be prepared by a user with a kit. For example, there may be provided a kit comprising as materials with a non-radiolabeled compound (i.e., a compound with or without the X-substituent). Optionally, the compound can be in a dry condition and, also optionally, one or more inert, pharmaceutically acceptable carriers and/or auxiliary substances may be added. A kit may also include materials such as a reducing agent and, optionally, a chelator. These materials may also be combined. The kit can comprise instructions for carrying out a method that involves reacting the materials with a detectable marker including, for example, $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$ or $^{99m}Tc$. An exemplary $^{99m}Tc$ detectable marker can be in the form of a pertechnetate solution that is, optionally, included with the kit. The detectable marker may also be included with the kit. The kit may also include instructions for performing an in vivo imaging protocol with an amyloid probe prepared as provided herein. The imaging of amyloid deposits may also be carried out quantitatively so that the amount of amyloid deposits can be determined. In one aspect, amyloid probes for imaging include a radioisotope such as $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$ or $^{76}Br$.

Exemplary probes or radiotracers known in the art may be used to study amyloid distributions via radioscintigraphy, magnetic resonance imaging (MRI), chemiluminescence, near infrared luminescence, fluorescence, spectroscopy, gamma imaging, magnetic resonance imaging, magnetic resonance spectroscopy, fluorescence spectroscopy, SPECT, computed tomography (CT scan), positron emission tomography (PET) or combinations thereof. Exemplary imaging protocols, means, devices, apparatuses or systems include those generally described in U.S. Pat. Nos. 6,072,177, 6,803,580, 5,900,636, 6,271,524 and 5,532,489, each of which is incorporated by reference herein.

Also included in the above embodiments, aspects and variations are salts of amino acids such as arginate and the like, gluconate, and galacturonate. Some of the compounds of the invention may form inner salts or Zwitterions. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution.

Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration.

Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa. In one variation, there is provided the above compound, or a pharmaceutically acceptable salt thereof, optionally in the form of a single stereoisomer or mixture of stereoisomers thereof.

In addition to the exemplary embodiments, aspects and variations described above, further embodiments, aspects and variations will become apparent by reference to the drawings and figures and by examination of the following descriptions.

BRIEF DESCRIPTION OF THE FIGURES

FIG. 1 depicts the measurement of aggregation prevention by added zinc and disaggregation of zinc induced aggregates by AC047 in a bisANS assay. In the presence of soluble Aβ, zinc induces aggregation within milliseconds. This aggregation is detected by an increase in bisANS fluorescence. An excess of EDTA serves as a control by binding zinc and preventing aggregation. Both prevention of aggregation and disaggregation can be detected in the assay. The dotted arrow indicates that AC047 can prevent zinc induced aggregation. The solid arrow indicated that AC047 can eliminate zinc induced Aß aggregates.

FIG. 2 depicts the prevention of Aß aggregation at compound concentrations ranging from 0.11 to 7.5 µM.

FIG. 3 depicts the elimination of Aß aggregates at compound concentrations ranging from 0.11 to 7.5 µM.

FIG. 4 depicts the calculated $EC_{50}$ concentrations for aggregation prevention by new compounds.

FIG. 5 depicts the calculated $EC_{50}$ concentrations for aggregation elimination by new compounds.

FIG. 6 depicts the copper Ionophore Assay on M17 Cells; Assays performed with 10 µM $CuSO_4$+10 µM Ionophore.

FIG. 7 depicts inhibition of ThT Assay by 5 µM Test Molecule.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $C_{1-20}$ alkyl (or $C_1$-$C_{20}$ alkyl), for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)_m$— group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $C_{1-20}$ alkyl, for example) and/or aryl group (as in $C_{5-10}$ aryl or $C_{6-10}$ aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a —$C_{1-3}$ alkylene- or —$C_{1-3}$ alkylenyl-.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partically saturated or aromatic.

"Halogen" or "halo" means fluorine, chlorine, bromine or iodine.

A "heterocyclyl" or "heterocycle" is a cycloalkyl wherein one or more of the atoms forming the ring is a heteroatom that is a N, O or S. A heterocyclyl includes aromatic heterocyclyl and non-aromatic heterocyclyl groups. Non-exclusive examples of heterocyclyl include oxazolyl, 4-imidazolyl, 5-imidazolyl, piperidyl, 4-morpholyl, 4-piperazinyl, pyrrolidinyl, 1,4-diazaperhydroepinyl, 1,3-dioxanyl, and the like.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like. Such salts may include base addition salts formed with inorganic bases such as lithium hydroxide, sodium hydroxide, potassium hydroxide etc. . . . .

"Therapeutically effective amount" means a drug amount that elicits any of the biological effects listed in the specification.

"Substituted or unsubstituted" or "optionally substituted" means that a group such as, for example, alkyl, aryl, heterocyclyl, $(C_{1-8})$cycloalkyl, hetrocyclyl($C_{1-8}$)alkyl, aryl($C_{1-8}$)alkyl, heteroaryl, heteroaryl($C_{1-8}$)alkyl, and the like, unless specifically noted otherwise, may be unsubstituted or may substituted by 1, 2 or 3 substituents selected from the group such as halo, trifluoromethyl, trifluoromethoxy, methoxy, carboxy, —$NH_2$, —$NO_2$, —OH, —SH, —SMe, —$NHCH_3$, —$N(CH_3)_2$, —CN and the like.

Experimental

The following procedures may be employed for the preparation of the compounds of the present invention. The starting materials and reagents used in preparing these compounds are either available from commercial suppliers such as the Sigma Aldrich Chemical Company, Bachem or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy and carboxy groups are described in Greene et al., *Protective Groups in Organic Synthesis*, Second Edition, John Wiley and Sons, New York, 1991.

In one variation, the compounds of formula I, where $A^1$ and $A^2$ are —C(O)—, can be synthesized by the steps outlined in Scheme 1.

SCHEME 1:

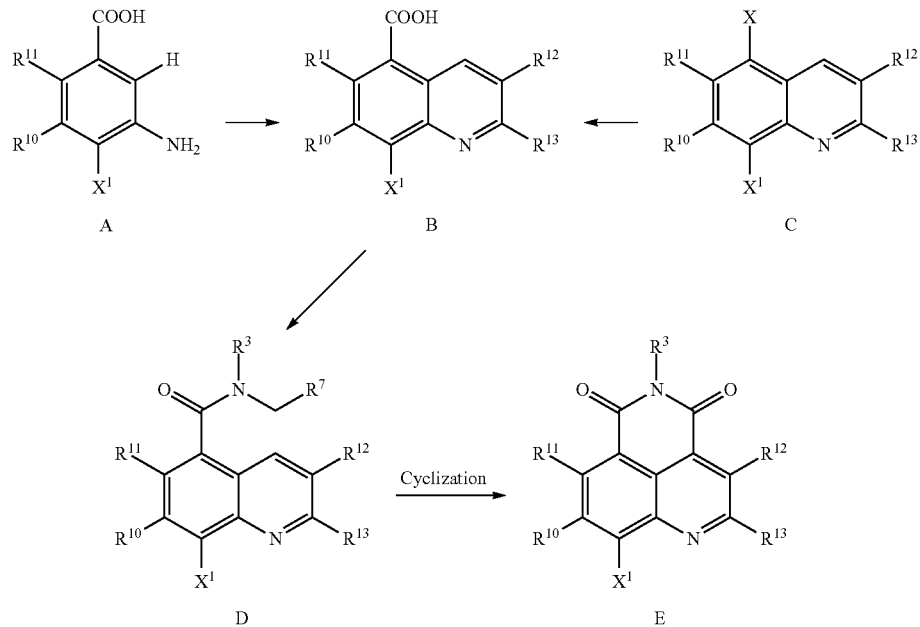

In one embodiment, the preparation of various 6-azaphenalene derivatives may be performed starting from a cyclization of a 3-amino-benzoic acid derivative A to form the 5-carboxyl quinoline derivative B. The cyclization reaction may be performed with glycerol with iodine, under acidic condition, such as with $H_2SO_4$. Alternatively, the quinoline derivative C may be converted to the corresponding 5-carboxyl quinoline derivative B. The carboxyl quinoline derivative may be converted to the corresponding carboxamide derivative D, which may undergo cyclization under basic condition to form the corresponding 6-azaphenalene derivative E. In one aspect, cyclization may be performed using a carbonate base in an organic solvent, such as potassium carbonate in DMF, or an organometallic base, such as LDA in an organic solvent, such as THF.

In another variation, the compounds of formula I, where $A^1$ and $A^2$ are —$CH_2$—, can be prepared by the steps outlined in Scheme 2.

Scheme 2:

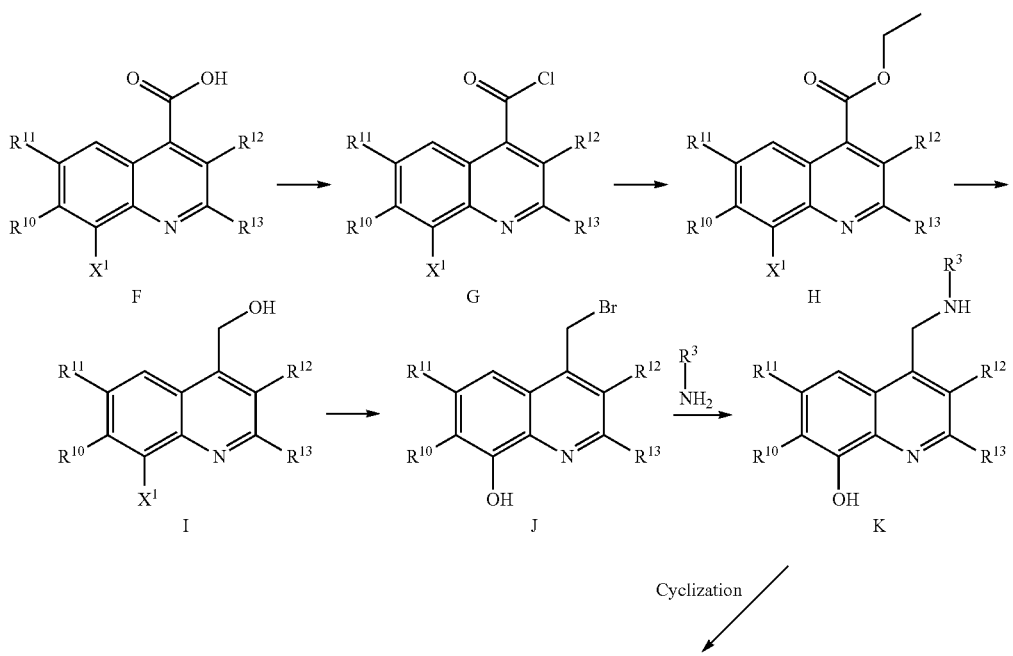

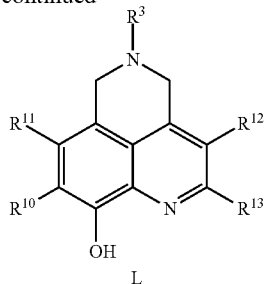

L

In another embodiment, these variants of 6-azaphenalene may be prepared according to Scheme 2 starting from 8-methoxyquiloline 4-carboxylic acid derivative F. The carboxylic acid derivative F may be converted to the acid chloride derivative G with a halogenating agent, such as an acid halide, such as thionyl chloride or the like. The quinoline derivative G may be converted to the ester H when treated with an alcohol, such as ethanol. Other simple esters related to H are also suitable when G is treated with simple alcohols such as n-butanol. The quinoline derivative H may be converted to the corresponding alcohol I using standard methods of reduction of esters to alcohols. The action of acidic conditions such as concentrated HBr may convert alcohol I to bromide J while simultaneously demethylating the methyl ether (converting $X^1$=OMe to $X^1$=OH). The bromide derivative J may be converted to the derivative K by reacting with an amine, such as benzylamine. The quinoline derivative K may undergo cyclization to the corresponding 6-azaphenalene derivative L. In one aspect, cyclization may be performed in aqueous formaldehyde using an organic solvent such as THF.

In another embodiment, the 6-azaphenalene acetal derivative M can be converted to the corresponding cyano-acrylate ester derivative N by treating the 6-azaphenalene acetal derivative with an alpha-cyano ester.

Scheme 4

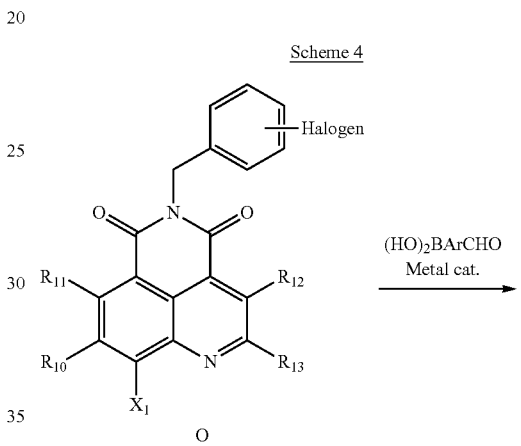

Scheme 3

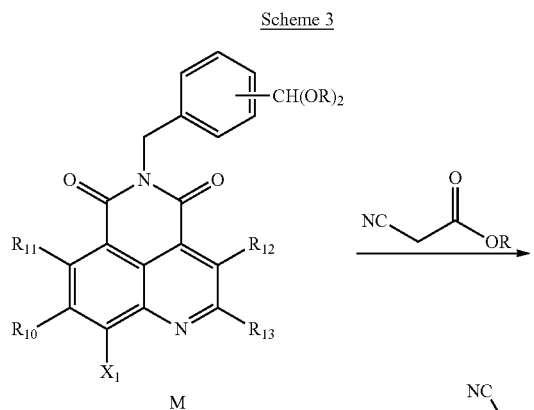

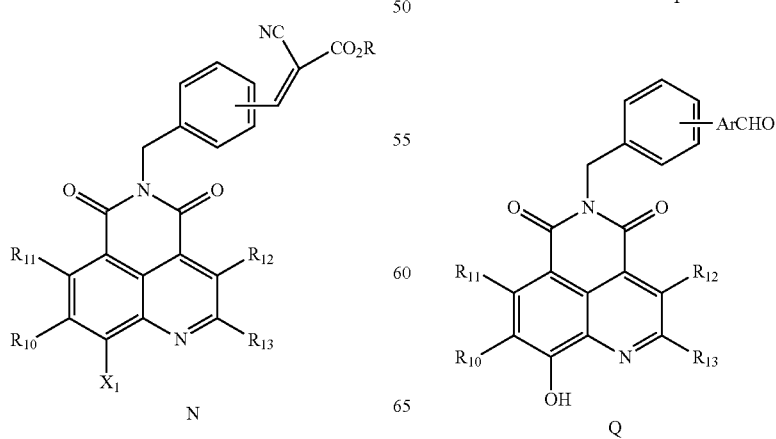

-continued

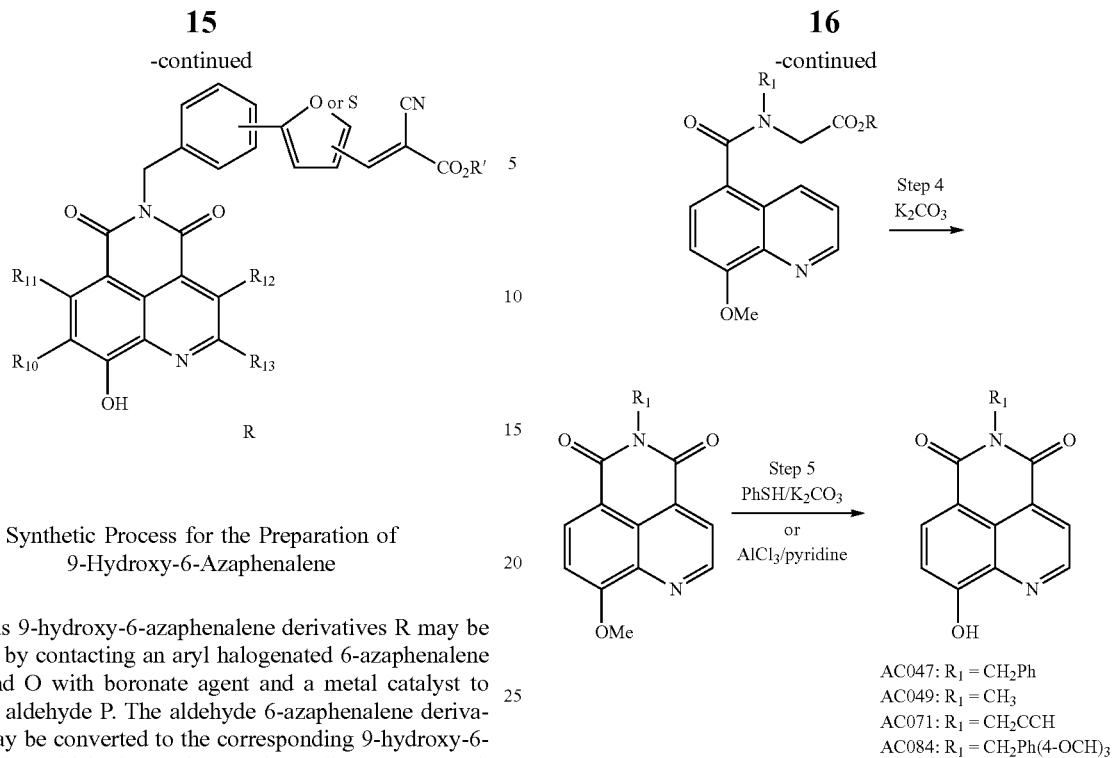

Synthetic Process for the Preparation of 9-Hydroxy-6-Azaphenalene

Various 9-hydroxy-6-azaphenalene derivatives R may be prepared by contacting an aryl halogenated 6-azaphenalene compound O with boronate agent and a metal catalyst to form the aldehyde P. The aldehyde 6-azaphenalene derivative P may be converted to the corresponding 9-hydroxy-6-azaphenalene aldehyde Q, where $X_1$ is an alkoxy group such as a methoxy group. Condensation of the 9-hydroxy-6-azaphenalene aldehyde Q with an alpha cyano ester affords the corresponding cyano-acrylate ester derivative R, wherein in the compound Q, "Ar" is a furan or a thiofuran.

Preparation of AC047, AC049, AC071 and AC084

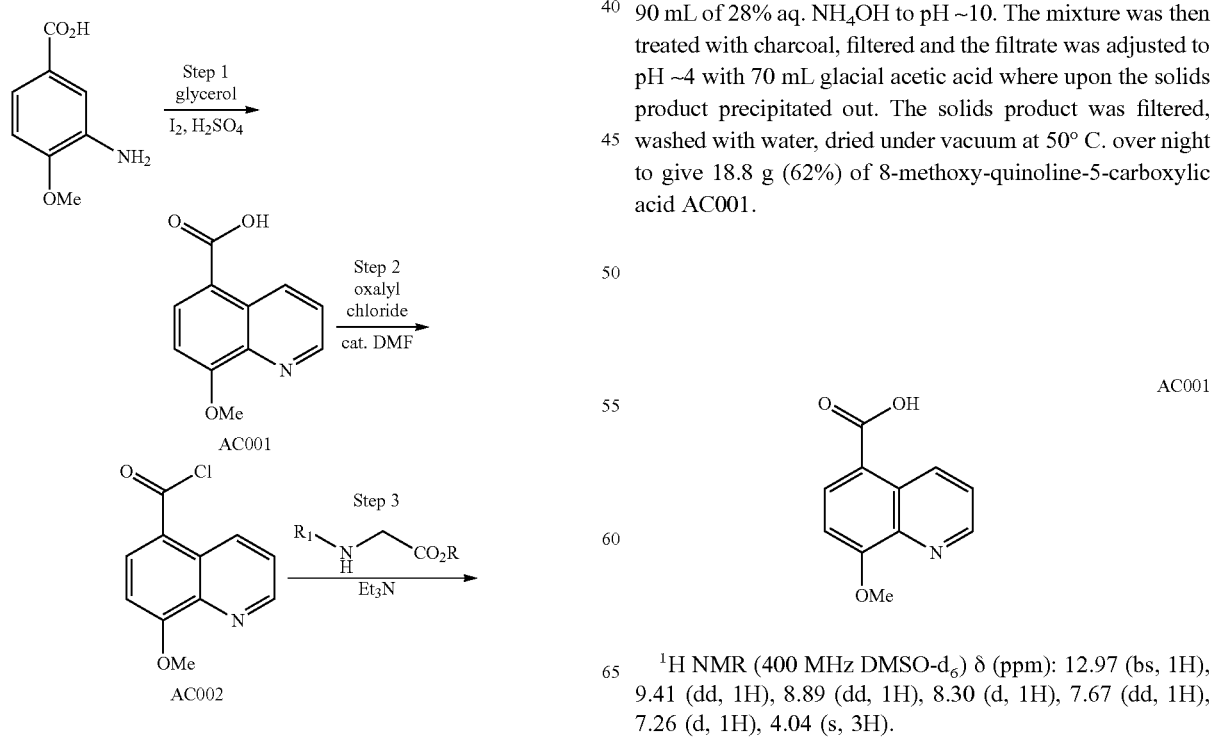

Step 1: Preparation of 8-methoxy-quinoline-5-carboxylic acid AC001
(*Org. Lett.* 2005, 17, 3673)

Reflux a mixture of 25 g 3-amino-4-methoxybenzoic acid, 0.72 g iodine, 20.8 g glycerol and 50 mL conc. $H_2SO_4$ for 2.5 hours (internal temperature at ~135° C.). After cooling to room temperature, 250 mL of water was added, followed by 90 mL of 28% aq. $NH_4OH$ to pH ~10. The mixture was then treated with charcoal, filtered and the filtrate was adjusted to pH ~4 with 70 mL glacial acetic acid where upon the solids product precipitated out. The solids product was filtered, washed with water, dried under vacuum at 50° C. over night to give 18.8 g (62%) of 8-methoxy-quinoline-5-carboxylic acid AC001.

$^1$H NMR (400 MHz DMSO-$d_6$) δ (ppm): 12.97 (bs, 1H), 9.41 (dd, 1H), 8.89 (dd, 1H), 8.30 (d, 1H), 7.67 (dd, 1H), 7.26 (d, 1H), 4.04 (s, 3H).

Step 2: Preparation of 8-methoxy-quinoline-5-carboxylic acid chloride (AC002; 119-108)

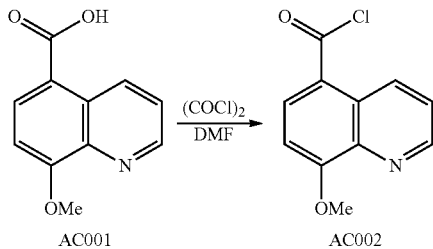

Step 2: Preparation of 8-methoxy-quinoline-5-carboxylic acid chloride AC002

To a slurry of 2 g 8-methoxy-quinoline-5-carboxylic acid AC001 in 35 mL $CH_2Cl_2$ at ~0° C. was added dropwise, via syringe, ~0.83 mL oxalyl chloride. A catalytic amount of DMF (~50 μL) was added. The mixture was held at room temperature for 1 hour. The mixture was evaporated to remove ca. 80% of the solvent. Methyl t-butyl ether was added to the residual solids which was then filtered and dried under vacuum to give 2.3 g (quantitative) of 8-methoxy-quinoline-5-carboxylic acid chloride AC002.

AC002

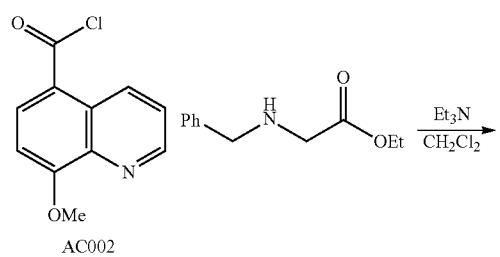

$^1H$ NMR (400 MHz DMSO-$d_6$) δ (ppm): 9.86 (dd, 1H), 9.11 (dd, 1H), 8.47 (d, 1H), 8.06 (dd, 1H), 7.55 (d, 1H), 4.16 (s, 3H).

Step 3: Preparation of ethyl 2-(N-benzyl-8-methoxyquinoline-5-carboxamido) acetate (AC024; 119-116)

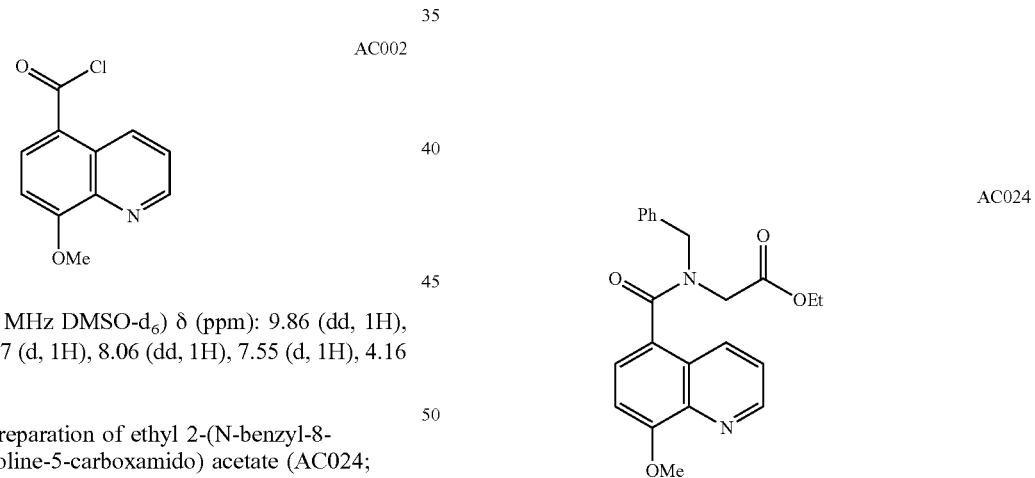

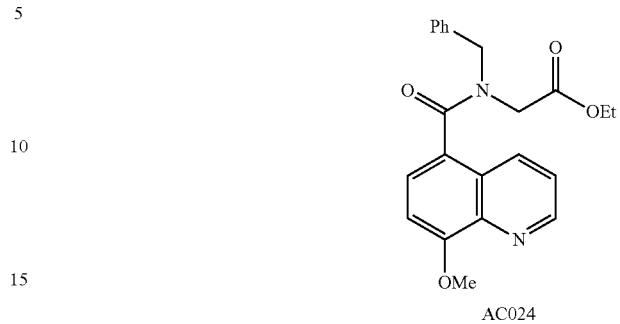

AC024

Dissolve 5.1 g N-benzyl-glycine ethyl ester in 100 mL $CH_2Cl_2$ and 13.7 mL $Et_3N$ to a clear solution. The solids 8-methoxyquinoline-5-carboxylic acid chloride (8.2 g) was added portionwise to the amine mixture at room temperature. The mixture was held at 20-40° C. over night. Water was added to quench the reaction. The organic phase was washed with 5% aq. AcOH, treated with charcoal, dried over $Na_2SO_4$, evaporatively remove the solvent to a solid residue. The solids residue was reslurried in MTBE/EtOAc, filter and dried under vacuum to give 3.3 g (2.94:1 isomer ratio) ethyl 2-(N-benzyl-8-methoxyquinoline-5-carboxamido)acetate AC024.

AC024

$^1H$ NMR (400 MHz DMSO-$d_6$) δ (ppm): 8.91 and 8.88 (m, 1H), 8.44 and 8.14 (dd, 1H), 7.65 and 7.61 (dd, 1H), 7.13 to 7.52 (m, 7H), 4.81 and 4.37 (bs, 2H), 4.20 and 3.88 (q, 2H), 3.96 and 3.98 (s, 3H), 1.25 and 0.96 (t, 3H); $^{13}C$ NMR (125 MHz, DMSO-$d_6$) δ (ppm): 169.94, 169.80, 169.11, 168.96, 155.95, 155.87, 149.52, 149.41, 139.46, 139.20, 137.04, 136.35, 133.26, 132.98, 128.62, 128.59, 128.17, 127.49, 127.45, 127.08, 125.93, 125.87, 125.22, 125.13, 124.91, 124.88, 122.66, 122.49, 107.45, 107.19, 60.91, 60.87, 55.85, 55.82, 52.99, 50.43, 49.15, 46.83, 14.11, 13.78.

Step 4: Preparation Naphthyridone (AC036)

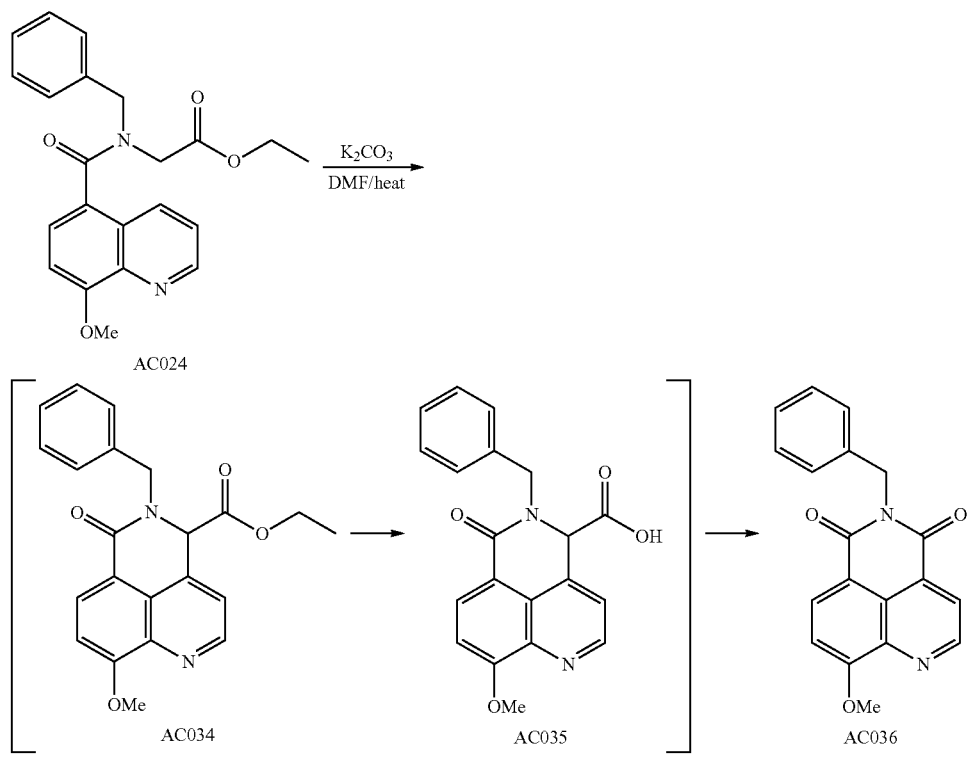

Step 4: Preparation of 5-benzyl-9-methoxy-4H-benzo[de][2,6]naphthyridine-4,6(5H)-dione AC036

A slurry of 6 g solids AC024 and 11 g solids $K_2CO_3$ (5 equiv.) in 120 mL DMF was heated to 100° C. for 70 hours. The solvent was then evaporatively removed, the residue was partitioned between water and dichloromethane. The organic phase was collected and dried over sodium sulfate, treated with activated charcoal, evaporated to a solids residue which was reslurried in MTBE/EtOAc/CH$_2$Cl$_2$, filtered, dried under vacuum at 60° C. to give 3.1 g of 5-benzyl-9-methoxy-4H-benzo[de][2,6]naphthyridine-4,6(5H)-dione, AC036.

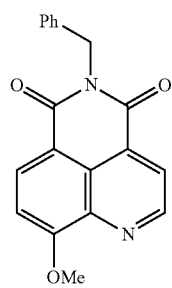
AC036

$^1$H NMR (400 MHz DMSO-d$_6$) δ (ppm): 9.21 (d, 1H), 8.52 (d, 1H), 8.32 (d, 1H), 7.55 (d, 1H), 7.16-7.43 (m, 5H), 5.23 (s, 2H), 4.14 (s, 3H); $^{13}$C NMR (125 MHz, DMSO-d$_6$) δ (ppm): 163.13, 162.31, 160.48, 150.56, 138.23, 137.16, 133.23, 129.11, 128.39, 127.58, 127.13, 123.48, 122.78, 113.83, 109.73, 56.69, 42.94.

Preparation of AC047: De-Methylation of AC036 with PhSH/K$_2$CO$_3$

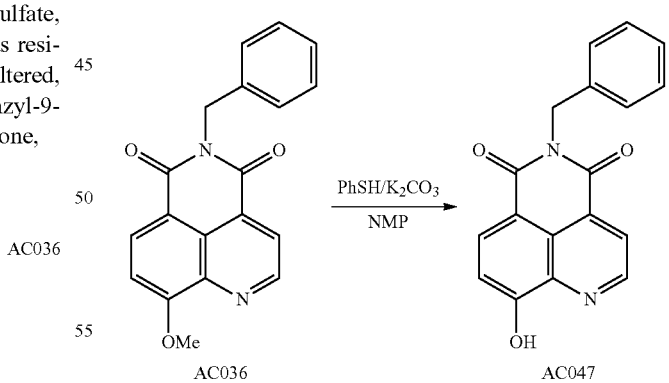

Step 5 (PhSH/K$_2$CO$_3$): Preparation of 5-benzyl-9-hydroxy-4H-benzo[de][2,6]naphthyridine-4,6(5H)-dione; AC047: De-Methylation of AC036 with PhSH/K$_2$CO$_3$ To a slurry of 0.1 g AC036 and 5 mg K$_2$CO$_3$ (0.05 equiv.) in 2 mL 1-methyl-2-pyrrolidinone was added 0.17 mL PhSH (1.05 equiv.). The mixture was heated to reflux and held for 30 minutes. After cooling to room temperature the reaction was quenched by adding 5% aq. NaOH to pH>12. The basic aqueous reaction mixture was washed with methylene chloride to remove organic materials, then acidified to pH 3-4 with 4N aq. HCl. Methylene chloride was added to the acidic aqueous phase whereupon solids product precipitated out. The solids were filtered from the biphasic slurry, washed with water, reslurried from MTBE/EtOAC, dried under vacuum at 50° C. to give 44 mg 5-benzyl-9-hydroxy-4H-benzo[de][2,6]naphthyridine-4,6(5H)-dione. AC047 (46% isolated yield).

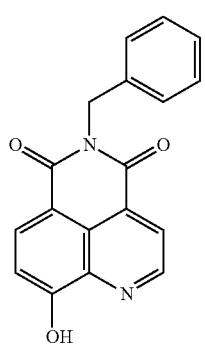

AC047

$^1$H NMR (400 MHz, DMSO-d$_6$) δ (ppm): 11.84 (br, OH), 9.20 (d, 1H), 8.41 (d, 1H), 8.31 (d, 1H), 7.38-7.20 (m, 6H), 5.22 (s, 2H); $^{13}$C NMR (125 MHz, DMSO-d$_6$) δ (ppm): 163.14, 162.30, 160.40, 149.70, 137.43, 137.25, 133.68, 129.24, 128.38, 127.55, 127.10, 123.87, 122.96, 113.65, 112.19, 42.87, 39.51.

Step 5: Alternative Procedure for the Preparation of AC047: De-Methylation of AC036 with AlCl$_3$/Pyridine

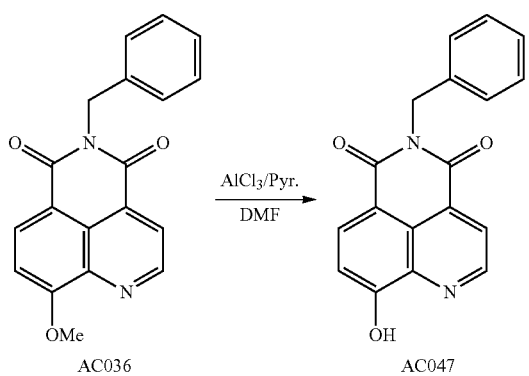

Step 5 (AlCl$_3$/Pyridine): Preparation of 5-benzyl-9-methoxy-4H-benzo[de][2,6]naphthyridine-4,6(5H)-dione AC047: De-Methylation of AC036 with AlCl$_3$/Pyridine To a slurry of 0.1 g AC036 in 2.5 mL DMF at ~0° C. was charged ~60 mg solids AlCl$_3$ (1.24 equiv.), followed by ~0.08 mL pyridine (3 equiv.). The reaction mixture was heated at 100° C. for 20 hours. After cooling to ~20° C., 0.18 mL conc. HCl was added to the reaction mixture, followed by ~2.02 mL water. The mixture was held at ~20° C. for 2 hours where it became a slurry. The slurry was filtered, washed with water, dried under vacuum at 60° C. over night to give 73 mg (77% yield) of 5-benzyl-9-methoxy-4H-benzo[de][2,6]naphthyridine-4,6(5H)-dione AC047.

Preparation of 18-F Derivative of AC086 from AC089

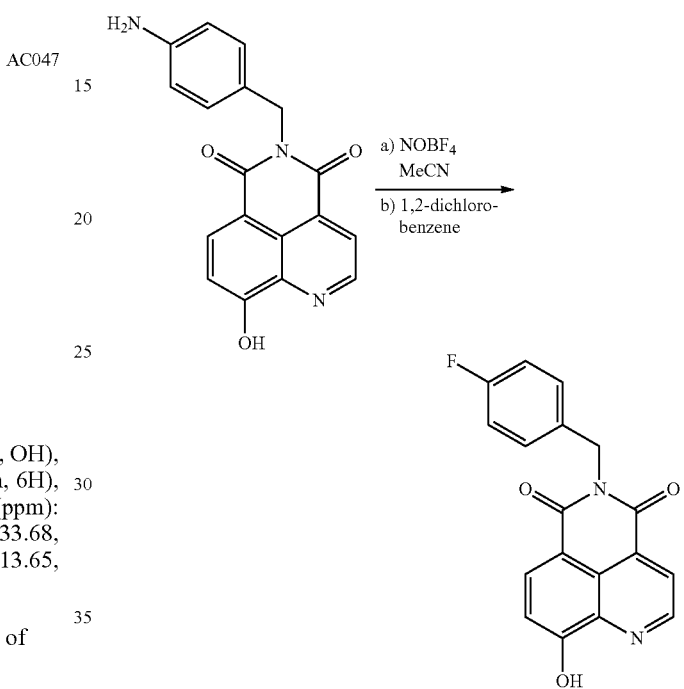

5-(4-aminobenzyl)-9-hydroxy-4H-benzo[de][2,6]naphthyridine-4,6(5H)-dione (20.6 mg) was suspended in anhydrous acetonitrile (0.16 mL) under N$_2$. This was cooled to 0° C. and nitrosyl tetrafluoroborate (9.8 mg) was added in one portion. The reaction was stirred at 0° C. for 1 hour. The solvent was removed in vacuo, and to the residue was added anhydrous 1,2-dichlorobenzene (0.86 mL). The mixture was heated to 160° C. for 1 hour, then cooled to room temperature and concentrated. The residue was purified via column chromatography on silica gel (0 to 5% methanol in dichloromethane) to afford 5-(4-fluorobenzyl)-9-hydroxy-4H-benzo[de][2,6]naphthyridine-4,6(5H)-dione (6.8 mg).

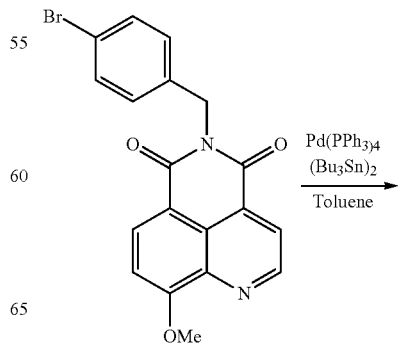

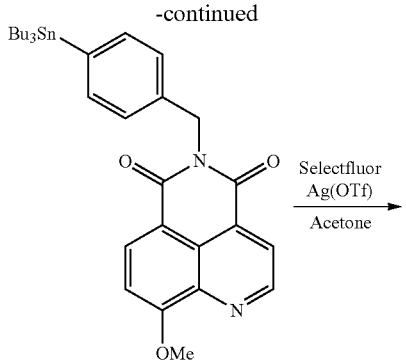

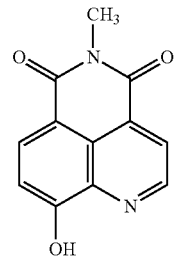

AC049

AC049: 9-Hydroxy-5-methyl-4H-benzo[de][2,6]naphthyridine-4,6(5H)-dione was similarly prepared according to Scheme 5.

¹H NMR (400 MHz, DMSO-d6) δ (ppm): 11.76 (br, OH), 9.19 (d, 1H), 8.39 (dd, 1H), 8.30 (d, 1H), 7.34 (dd, 1H), 3.37 (s, 3H); ¹³C NMR (125 MHz, DMSO-d₆) δ (ppm): 163.25, 162.50, 160.08, 149.64, 137.35, 133.25, 129.33, 123.62, 122.61, 113.49, 112.46, 26.64.

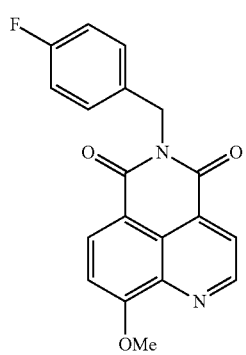

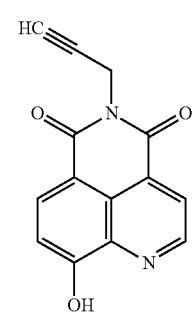

AC071

A flame-dried and nitrogen purged flask fitted with a reflux condenser was charged with 5-(4-bromobenzyl)-9-methoxy-4H-benzo[de][2,6]naphthyridine-4,6(5H)-dione (0.10 g), hexabutylditin (0.26 mL) and tetrakis(triphenylphosphine)palladium (0.015 g). The reaction set-up was purged with nitrogen for an additional 10 minutes. Anhydrous, nitrogen sparged toluene (2.54 mL) was added and the reaction heated at reflux for 17 hours. The reaction was allowed to cool to room temperature and diluted with dichloromethane (10 mL). The organic layer was washed with water (10 mL) and the aqueous wash extracted with dichloromethane (3×10 mL). The combined organic layer was dried over magnesium sulfate, filtered and concentrated. The residue was purified via column chromatography on silica gel (30 to 80 ethyl acetate in hexanes containing 1% triethylamine) to afford 9-methoxy-5-(4-(tributylstannyl)benzyl)-4H-benzo[de][2,6]naphthyridine-4,6(5H)-dione (0.082 g).

¹H-NMR (400 MHz, CDCl₃) δ 9.19 (d, 1H), 8.58 (d, 1H), 8.33 (d, 1H), 7.46 (d, 2H), 7.38 (d, 2H), 7.26 (d, 1H), 5.31 (s, 2H), 4.20 (s, 3H), 1.52-1.42 (m, 6H), 1.32-1.21 (m, 6H), 1.01-0.94 (m, 6H), 0.81 (t, 9H). LRMS: 609.21 (M+H)⁺

To a N₂-filled flask containing the 9-methoxy-5-(4-(tributylstannyl)benzyl)-4H-benzo[de][2,6]naphthyridine-4,6(5H)-dione (19.9 mg) was added Selectfluor (11.6 mg) and AgOTf (16.8 mg). To this was added anhydrous, nitrogen-sparged acetone (0.66 mL). After 20 min at room temperature the reaction was concentrated in vacuo. The residue was purified via column chromatography on silica gel (0 to 4% methanol in dichloromethane) to afford 5-(4-fluorobenzyl)-9-methoxy-4H-benzo[de][2,6]naphthyridine-4,6(5H)-dione (7.7 mg).

AC071: 9-Hydroxy-5-(prop-2-yn-1-yl)-4H-benzo[de][2,6]naphthyridine-4,6(5H)-dione was similarly prepared according to Scheme 5.

¹H NMR (400 MHz, DMSO-d6) δ (ppm): 8.48 (dd, 1H), 8.95 (dd, 1H), 8.18 (dd, 1H), 7.87 (m, 1H), 7.50 (m, 1H), 7.27 (dd, 1H), 6.68 (m, 1H); ¹³C NMR (125 MHz, DMSO-d6) δ (ppm): 161.50, 157.76, 148.48, 136.98, 133.71, 129.81, 128.71, 121.98, 120.53, 115.64, 114.52, 113.49, 113.14, 99.49.

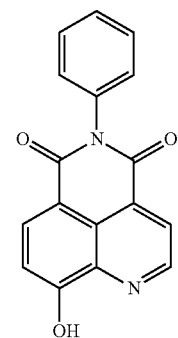

AC062: ¹H NMR (DMSO-d6, 400 MHz): δ 9.19 (d, J=4.4 Hz, 1H), 8.37 (d, J=8.3 Hz, 1H), 8.28 (d, J=4.4 Hz, 1H), 7.36-7.51 (m, 3H), 7.34 (m, 3H). MS (m/z): 291 (M+1).

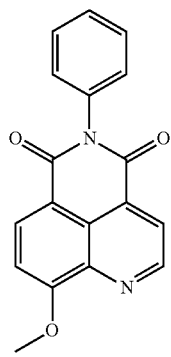 [SMILES: COc1ccc2c3c(ccnc13)C(=O)N(c1ccccc1)C2=O]

AC075: ¹H NMR (CDCl₃, 400 MHz): δ 9.24 (d, J=4.4 Hz, 1H), 8.61 (d, J=8.3 Hz, 1H), 8.37 (d, J=4.4 Hz, 1H), 7.53 (m, 3H), 7.29 (m, 3H), 4.23 (s, 3H). MS (m/z): 305 (M+1).

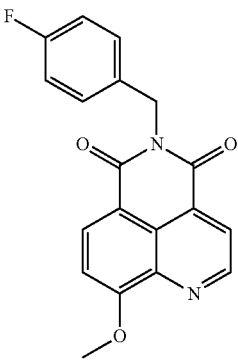 [SMILES: COc1ccc2c3c(ccnc13)C(=O)N(Cc1ccc(F)cc1)C2=O]

AC085: ¹H NMR (CDCl₃, 400 MHz): δ 9.20 (d, J=4.4 Hz, 1H), 8.57 (d, J=8.3 Hz, 1H), 8.33 (d, J=4.4 Hz, 1H), 7.51 (m, 2H), 7.26 (d, J=8.3 Hz, 1H), 6.97 (m, 2H), 5.29 (s, 2H), 4.20 (s, 3H). MS (m/z): 337 (M+1).

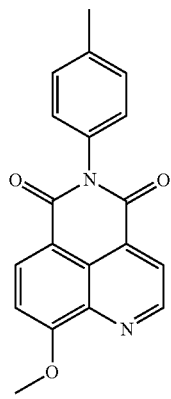

AC076: ¹H NMR (CDCl₃, 400 MHz): δ 9.23 (d, J=4.4 Hz, 1H), 8.60 (d, J=8.3 Hz, 1H), 8.36 (d, J=4.4 Hz, 1H), 7.33 (d, J=8.3 Hz, 2H), 7.29 (d, J=8.3 Hz, 1H), 7.15 (d, J=6.4 Hz, 2H), 4.23 (s, 3H), 2.42 (s, 3H). MS (m/z): 319 (M+1).

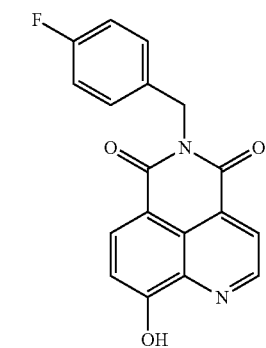

AC086: ¹H NMR (DMSO-d6, 400 MHz): δ 11.83 (br s, 1H), 9.18 (d, J=4.4 Hz, 1H), 8.39 (d, J=8.3 Hz, 1H), 8.29 (d, J=4.4 Hz, 1H), 7.40 (m, 2H), 7.33 (d, J=8.3 Hz, 1H), 7.11 (m, 2H), 5.18 (s, 2H). MS (m/z): 323 (M+1).

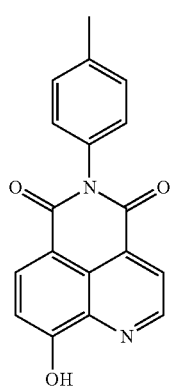

AC077: ¹H NMR (DMSO-d6, 400 MHz): δ 9.19 (d, J=3.9 Hz, 1H), 8.37 (d, J=8.3 Hz, 1H), 8.28 (d, J=4.4 Hz, 1H), 7.35 (d, J=8.3 Hz, 1H), 7.30 (d, J=8.3 Hz, 2H), 7.22 (d, J=8.3 Hz, 2H), 2.38 (s, 3H). MS (m/z): 305 (M+1).

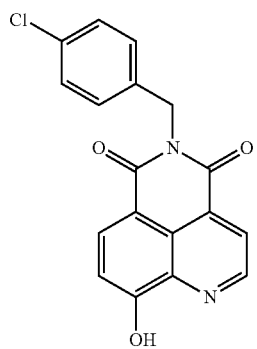 [SMILES: O=C1c2ccnc3c(O)ccc(c23)C(=O)N1Cc1ccc(Cl)cc1]

AC087: ¹H NMR (DMSO-d6, 400 MHz): δ 11.94 (br s, 1H), 9.18 (d, J=4.4 Hz, 1H), 8.39 (d, J=8.3 Hz, 1H), 8.29 (d, J=4.4 Hz, 1H), 7.35 (m, 5H), 5.18 (s, 2H). MS (m/z): 339 (M+1).

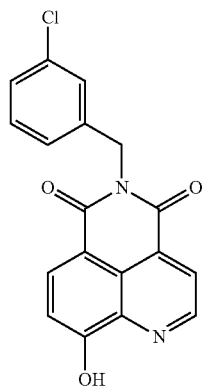 [SMILES: O=C1c2ccnc3c(O)ccc(c23)C(=O)N1Cc1cccc(Cl)c1]

AC088: $^1$H NMR (DMSO-d6, 400 MHz): δ 9.16 (d, J=4.4 Hz, 1H), 8.38 (d, J=8.3 Hz, 1H), 8.28 (d, J=4.4 Hz, 1H), 7.42 (s, 1H), 7.31 (m, 4H), 5.19 (s, 2H). MS (m/z): 339 (M+1).

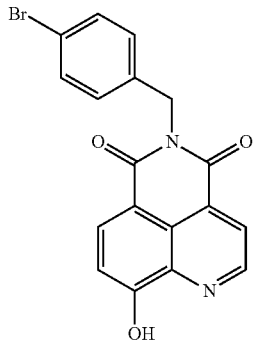

AC089: $^1$H NMR (DMSO-d6, 400 MHz): δ 9.18 (d, J=4.4 Hz, 1H), 8.39 (d, J=8.3 Hz, 1H), 8.29 (d, J=4.4 Hz, 1H), 7.48 (m, 2H), 7.32 (m, 3H), 5.17 (s, 2H). MS (m/z): 384 (M+1).

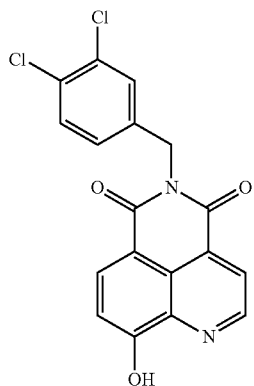 [SMILES: O=C1c2ccnc3c(O)ccc(c23)C(=O)N1Cc1ccc(Cl)c(Cl)c1]

AC092: $^1$H NMR (DMSO-d6, 400 MHz): δ 9.18 (d, J=4.4 Hz, 1H), 8.39 (d, J=8.3 Hz, 1H), 8.29 (d, J=4.4 Hz, 1H), 7.65 (d, J=2.0 Hz, 1H), 7.55 (d, J=8.3 Hz, 1H), 7.34 (m, 2H), 5.18 (s, 2H). MS (m/z): 371 (M−1).

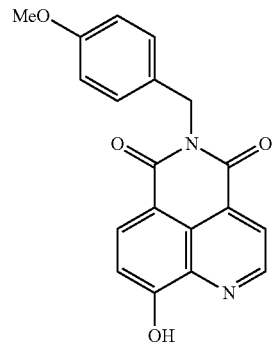

AC084: 9-Hydroxy-5-(4-methoxybenzyl)-4H-benzo[de][2,6]naphthyridine-4,6(5H)-dione was similarly prepared according to Scheme 5.

$^1$H NMR (400 MHz, DMSO-d$_6$) δ (ppm): 9.19 (dd, 1H), 8.40 (dd, 1H), 8.30 (dd, 1H), 7.33 (m, 3H), 6.85 (m, 2H), 5.14 (s, 2H), 3.69 (s, 3H).

Preparation of BC098 and BC108

Compound BC098 and BC108 were prepared according to Steps 1-4 of Scheme 5, followed by Steps 5A and 6 shown in Scheme 6.

Scheme 6: Preparation of 8-hydroxynaphthyridinone analogues. (BC098, BC108)

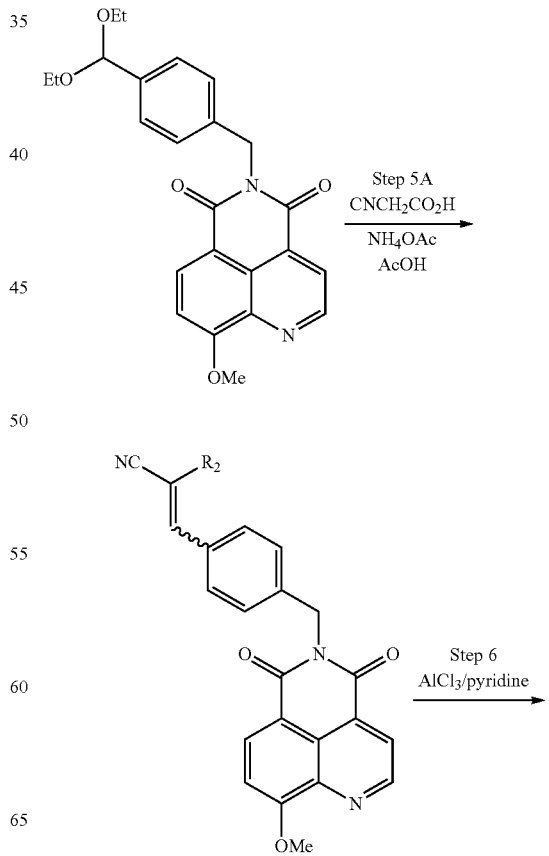

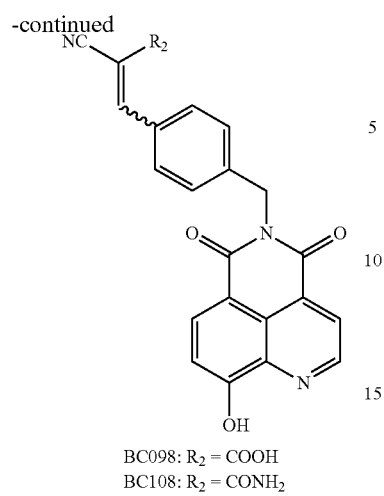

BC098: R$_2$ = COOH
BC108: R$_2$ = CONH$_2$

Step 5A

Crude acetal (1 equiv.), ammonium acetate (3 equiv.) and cyanoacetic acid (2.4 equiv.) was heated to 130° C. in 4 mL glacial acetic acid for 4 hours. Water was then added to the coll reaction mixture. The solids precipitate was filtered and washed with water, dried under vacuum at 50-60° C. over night to give the desired condensed nitrile acrylic acid derivative intermediate.

Step 6

The condensed nitrile acrylic acid derivative intermediate (1 equiv.) and AlCl$_3$ (2.5 equiv.), pyridine (6 equiv.) was heated to 95° C. in DMF for 13 hours. Aqueous HCl was added to the cool mixture. The solids precipitated was filtered, washed with water, dried under vacuum at 50-60° C. over night to give the desired product.

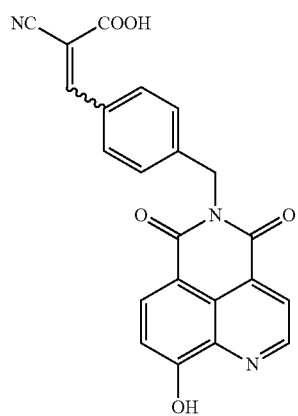

BC098: 2-Cyano-3-(4-((9-hydroxy-4,6-dioxo-4H-benzo[de][2,6]naphthyridin-5(6H)-yl)methyl)phenyl)acrylic acid $^1$H NMR (400 MHz, DMSO-d$_6$) δ (ppm): 9.96 (b, OH), 9.21 (d, 1H), 8.42 (d, 1H), 8.31 (m, 2H), 7.97 (d, 2H), 7.54 (d, 2H), 7.37 (d, 1H), 5.29 (s, 2H); $^{13}$C NMR (125 MHz, DMSO-d$_6$) δ (ppm): 163.80, 163.76, 162.86, 160.96, 150.19, 143.34, 130.81, 128.47, 123.45, 112.74, 103.84, 43.41.

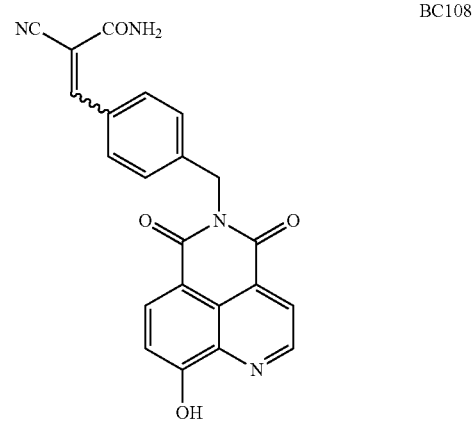 [SMILES: N#CC(=Cc1ccc(CN2C(=O)c3ccnc4c(O)ccc(c34)C2=O)cc1)C(N)=O]

BC108: 2-Cyano-3-(4-((9-hydroxy-4,6-dioxo-4H-benzo[de][2,6]naphthyridin-5(6H)-yl)methyl)phenyl)acrylamide $^1$H NMR (400 MHz, DMSO-d$_6$) δ (ppm): 11.85 (b, OH), 9.21 (d, 1H), 8.42 (d, 1H), 8.32 (d, 1H), 8.14 (s, 1H), 7.91 (b, NH), 7.87 (d, 2H), 7.75 (b, NH), 7.53 (d, 2H), 7.37 (d, 1H); 5.29 and 5.21 (2 s, 2H); $^{13}$C NMR (125 MHz, DMSO-d$_6$) δ (ppm): 163.23, 162.73, 162.33, 160.44, 150.23, 149.68, 141.91, 137.44, 133.69, 130.71, 130.15, 129.32, 127.97, 123.99, 122.95, 116.48, 113.62, 112.22, 106.31, 42.85.

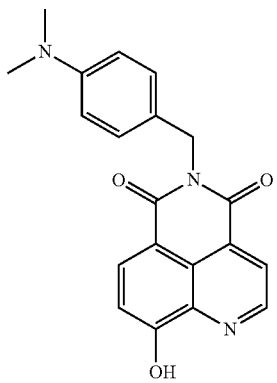 [SMILES: CN(C)c1ccc(CN2C(=O)c3ccnc4c(O)ccc(c34)C2=O)cc1]

AC107: $^1$H NMR (DMSO-d6, 400 MHz): δ 9.17 (d, J=4.4 Hz, 1H), 8.39 (d, J=7.8 Hz, 1H), 8.28 (d, J=4.4 Hz, 1H), 7.33 (d, J=8.2 Hz, 1H), 7.23 (d, J=8.8 Hz, 2H), 6.67 (d, J=7.4 Hz, 2H), 5.09 (s, 2H), 2.83 (s, 6H). MS (m/z): 348 (M+1).

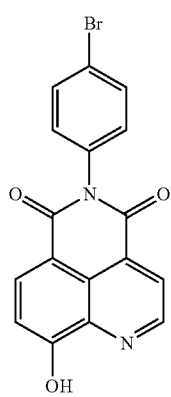 [SMILES: O=C1c2ccnc3c(O)ccc(c23)C(=O)N1c1ccc(Br)cc1]

AC113: ¹H NMR (DMSO-d6, 400 MHz): δ 9.15 (d, J=4.4 Hz, 1H), 8.34 (d, J=8.3 Hz, 1H), 8.26 (d, J=4.4 Hz, 1H), 7.71 (m, 2H), 7.33 (m, 2H), 7.26 (d, J=8.3 Hz, 1H). MS (m/z): 370 (M+1).

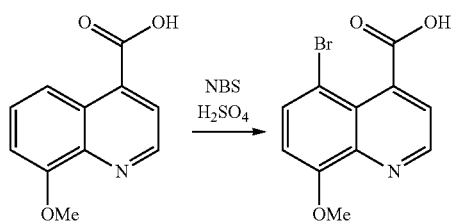 [SMILES: COc1cccc2c(C(=O)O)ccnc12 ; COc1ccc(Br)c2c(C(=O)O)ccnc12]

8-Methoxyquinoline 4-carboxylic acid (2.26 g) was dissolved in 98% sulfuric acid (40.5 mL) and N-Bromosuccinimide (1.98 g) added in one portion and the solution stirred at room temperature for 18 hours. The reaction was poured into to water (100 mL) and cooled to 0° C. in an ice bath. Water (100 mL) was added and the solution neutralized with saturated ammonium hydroxide solution (approx. 120 mL) until pH 8-9. Acetic acid was added until pH 4 and the precipitate collected via filtration. The brown precipitate was dried under vacuum overnight at 70° C. to yield 5-bromo-8-methoxyquinoline-4-carboxylic acid (2.69 g).

¹H NMR (400 MHz, DMSO-d6) δ 8.70 (d, 1H), 7.73 (d, 1H), 7.24 (d, 1H), 7.05 (d, 1H), 3.93 (s, 3H).

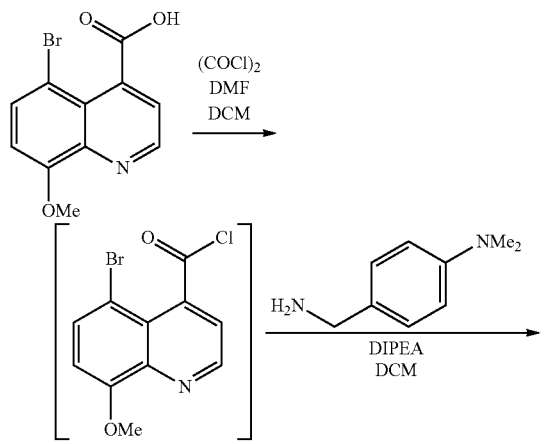

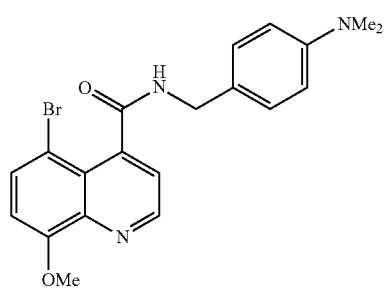

To a suspension of 5-bromo-8-methoxyquinoline 4-carboxylic acid (0.68 g) in anhydrous dichloromethane (9.64 mL) was added oxalyl chloride (1.02 mL). Anhydrous N,N-dimethylformamide (0.01 mL) was added and the reaction stirred at room temperature for 3 hours, then the solvent removed in vacuo. Anhydrous dichloromethane (10 mL) was added to the residue and the solvent removed in vacuo. Anhydrous dichloromethane (6.6 mL) was added to the residue and N,N-diisopropylethylamine (1.68 mL) added dropwise. The resulting solution was cooled to 0° C. and a solution of 4-(dimethylamino)benzylamine (0.36 g) in dichloromethane (3.0 mL) added dropwise. The reaction was allowed to warm to room temperature overnight. The reaction was quenched with water (10 mL) and saturated sodium bicarbonate solution (20 mL). The organic layer was separated and the aqueous layer extracted with dichloromethane (3×30 mL). The combined organic was washed with brine, dried over magnesium sulfate, filtered and concentrated. The residue was purified via chromatography on silica gel (0 to 4% methanol in dichloromethane) to afford 5-bromo N-(4-(dimethylamino)benzyl)-8-methoxyquinoline-4-carboxamide (0.77 g).

¹H NMR (400 MHz, CDCl₃) δ 8.90 (d, 1H), 7.79 (d, 1H), 7.48 (d, 1H), 7.26 (d, 2H), 6.94 (d, 1H), 6.69 (d, 2H), 5.91 (broad t, 1H), 4.80-4.35 (broad d, 2H), 4.06 (s, 3H), 2.92 (s, 6H).

tert-Butyl(4-((5-bromo-8-methoxyquinoline-4-carboxamido)methyl)phenyl) carbamate was similarly prepared.

¹H NMR (400 MHz, CDCl₃) δ 8.87 (d, 1H7.76 (d, 1H), 7.44 (d, 1H), 7.36-7.27 (m, 4H), 6.92 (d, 1H), 6.49 (s, 1H), 6.13 (broad t, 1H), 4.80-4.40 (broad d, 2H), 4.05 (s, 3H), 1.49 (s, 9H).

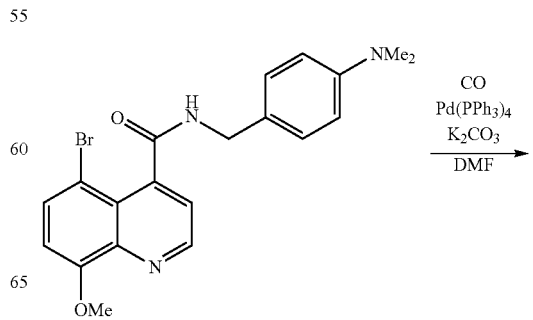

33
-continued

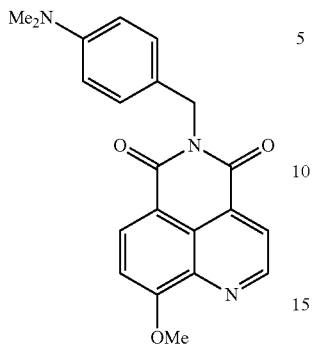

A 20 mL microwave vial was charged with 5-bromo-N-(4-(dimethylamino)benzyl)-8-methoxyquinoline-4-carboxamide (0.38 g), powdered potassium carbonate (0.25 g) and tetrakis(triphenylphosphine) palladium (0.05 g). The vial was purged with nitrogen for 15 minutes then anhydrous N,N-dimethylformamide (9.2 mL) was added. Carbon monoxide was bubbled through the solution for 15 minutes, the vial sealed, and carbon monoxide bubbled through the solution for an additional 15 minutes. The reaction was heated to 120° C. for 12 hours before being cooled t to room temperature. The solvent was removed in vacuo, the residue dissolved in dichloromethane (75 mL) and the organic phase washed with water (2×25 mL). The organic layer was dried over magnesium sulfate, filtered and concentrated. The residue was purified via chromatography on silica gel (0 to 5% methanol in dichloromethane) to afford 5-(4-(dimethylamino)benzyl)-9-methoxy-4H-benzo[de][2,6]naphthyridine-4,6(5H)-dione (0.22 g).

$^1$H-NMR (400 MHz, CDCl$_3$) δ 9.18 (d, 1H), 8.57 (d, 1H), 8.32 (d, 1H), 7.46 (broad d, 2H), 7.25 (d, 1H), 6.65 (broad d, 2H), 5.25 (s, 2H), 4.20 (s, 3H), 2.89 (s, 6H).

tert-Butyl(4-((9-methoxy-4,6-dioxo-4H-benzo[de][2,6]naphthyridin-5(6H)-yl)methyl)phenyl)carbamate was similarly prepared.

$^1$H-NMR (400 MHz, CDCl$_3$) δ 9.19 (d, 1H), 8.57 (d, 1H), 8.32 (d, 1H), 7.46 (d, 2H), 7.29-7.23 (m, 3H), 6.40 (broad s, 1H), 5.27 (s, 2H), 4.20 (s, 3H), 1.46 (s, 9H).

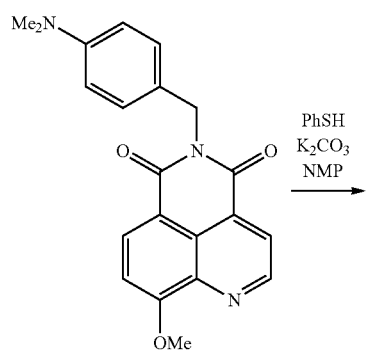

34
-continued

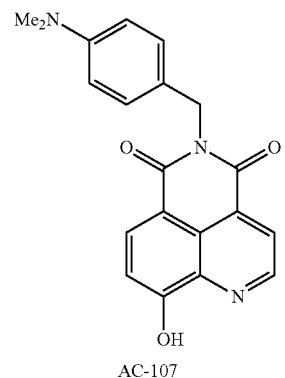
AC-107

5-(4-(dimethylamino)benzyl)-9-methoxy-4H-benzo[de][2,6]naphthyridine-4,6(5H)-dione (0.23 g) was dissolved in 1-methyl-2-pyrrolidinone (6.25 mL) and potassium carbonate (0.086 g) and thiophenol (0.13 mL) added. The reaction was heated to 170° C. for 1.5 hours before being cooled to room temperature. The reaction was poured into 3N hydrochloric acid (20 mL) and this washed with dichloromethane (3×20 mL). The combined organic washes were extracted with 3N hydrochloric acid (2×10 mL). The combined aqueous was neutralized to pH=5 with 2N aqueous sodium hydroxide and extracted with dichloromethane (3×40 mL). The combined organic extracts were dried over sodium sulfate, filtered, and concentrated. The residue was purified via chromatography on silica gel (0 to 4% methanol in dichloromethane) to afford 5-(4-(dimethylamino)benzyl)-9-hydroxy-4H-benzo[de][2,6]naphthyridine-4,6(5H)-dione (0.12 g).

$^1$H-NMR (400 MHz, DMSO-d6) δ 11.8 (s, 1H), 9.18 (d, 1H), 8.14 (d, 1H), 8.29 (d, 1H), 7.34 (d, 1H), 7.21 (d, 2H), 6.62 (d, 2H), 5.08 (d, 2H), 2.81 (s, 6H). LRMS: 348.11 (M+H)$^+$.

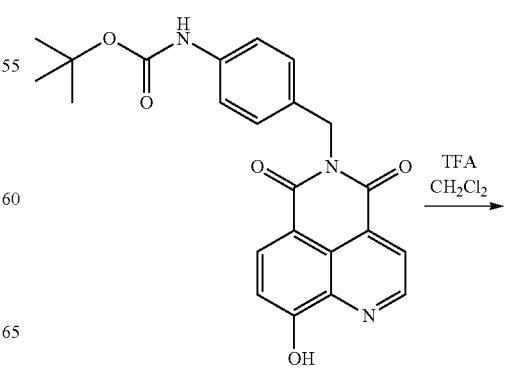

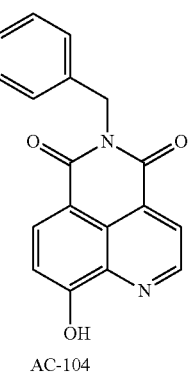

AC-104 tert-Butyl(4-((9-methoxy-4,6-dioxo-4H-benzo[de][2,6]naphthyridin-5 (6H)-yl)methyl)phenyl)carbamate (0.18 g) was dissolved in 1-methyl-2-pyrrolidinone (4.17 mL) and potassium carbonate (0.14 g) and thiophenol (0.21 mL) added. The reaction was heated to 170° C. for 1.5 hours before being cooled to room temperature and the solvent removed in vacuo. The residue was dissolved in dichloromethane (2.1 mL) and trifluoroacetic acid (2.1 mL) and this stirred at room temperature for 40 minutes. The reaction was poured into 1M hydrochloric acid (40 mL) and washed with ethyl acetate (3×20 mL). The combined organic was extracted with 1M hydrochloric acid (20 mL). To the combined aqueous was added saturated aqueous ammonium hydroxide until pH 8. The aqueous was acidified to pH 5 with acetic acid and extracted with dichloromethane (4×30 mL) and the combined organic dried over sodium sulfate, filtered and concentrated. The residue was purified via chromatography on silica gel (0 to 5% methanol in dichloromethane) to afford 5-(4-aminobenzyl)-9-hydroxy-4H-benzo[de][2,6]naphthyridine-4,6(5H)-dione (0.093 g). $^1$H-NMR (400 MHz, DMSO-d6) δ 9.17 (d, 1H), 8.39 (d, 1H), 8.29 (d, 1H), 7.32 (d, 1H), 7.06 (d, 2H), 6.45 (d, 2H), 5.02 (s, 2H). MS (m/z) 320.08 (M+H)$^+$

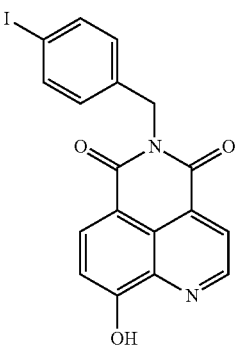

AC114: $^1$H NMR (DMSO-d6, 400 MHz): δ 9.17 (d, J=4.4 Hz, 1H), 8.38 (d, J=8.3 Hz, 1H), 8.28 (d, J=4.4 Hz, 1H), 7.63 (d, J=8.8 Hz, 2H), 7.33 (d, J=7.8 Hz, 1H), 7.15 (d, J=8.3 Hz, 2H), 5.14 (s, 2H). MS (m/z): 431 (M+1).

Synthetic Procedure for Preparing 5,6-dihydro-4H-benzo[de][2,6]naphthyridin-9-ols Preparation of Methyl 8-methoxyquinoline 4-carboxylate

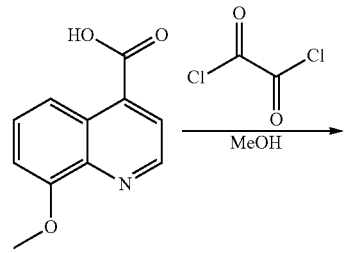

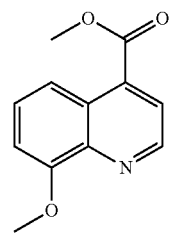

Methyl 8-methoxyquinoline-4-carboxylate: 1.7 grams of 8-methoxyquinoline-4-carboxylic acid was suspended in 200 ml of methylene chloride and cooled to 5 to 10° C. 10.0 ml of oxalyl chloride was added drop wise over 20 min. After the addition was complete the mixture was allowed to come to room temperature and stir for 2 hrs. The mixture was evaporated to remove the excess oxalyl chloride. The solid was dissolved in methylene chloride and added slowly to 150 ml of methanol that was cooled to 10° C. After the addition was completed, the mixture was allowed to come to room temperature and stir for 1 hr. The mixture was evaporated to a tacky solid. The solid residue was dissolved in 200 ml of methylene chloride and washed with saturated sodium bicarbonate. The methylene chloride solution was dried over sodium sulfate and evaporated to a dark oil. The oil crystallized on standing to give 11.8 grams (94%) of tan solid.

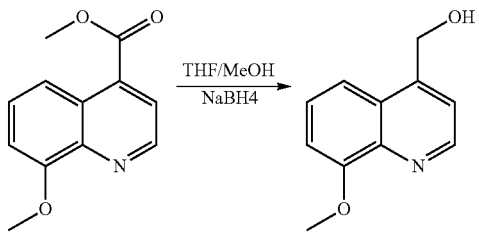

8-Methoxyquinolin-4-yl methanol: 4.0 grams of methyl 8-methoxyquinoline-4-carboxylate was dissolved in 200 ml of THF in a 1 liter round bottom flask. 4.16 grams of granulated sodium borohydride was added and the mixture was heated to about 65 to 70° C. After 15 min. methanol was cautiously added drop wise (20 ml over 30 min). The reaction was heated an additional 15 min. The reaction was cooled to 10° C. and quenched with a saturated solution of ammonium chloride. The mixture was extracted with ethyl acetate. The ethyl acetate was dried over sodium sulfate and evaporated to give 3.02 grams of a tan solid.

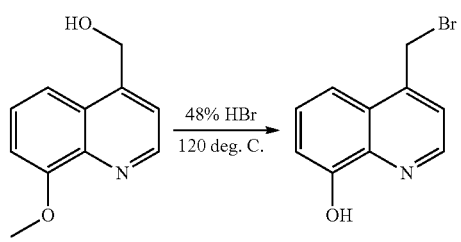

4-(Bromomethyl)quinolin-8-ol: 2.96 Grams of (8-methoxyquinolin-4-yl)methanol was dissolved in 30 ml of 48% HBr under nitrogen. The mixture was heated to 125° C. for 32 hrs. The reaction mixture was cooled to room temperature and carefully added to a solution of 40 grams of sodium bicarbonate. The resulting solid was collected and air dried to give 3.17 grams (85%) of a grey solid.

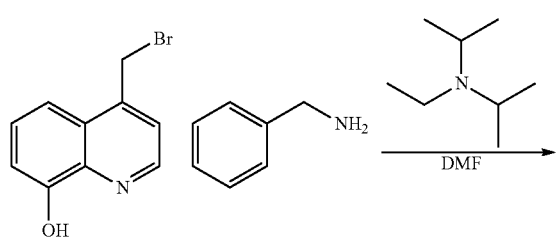

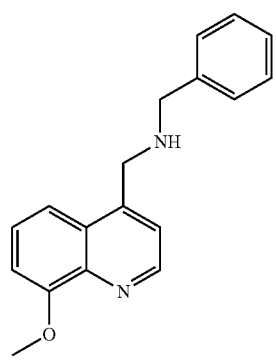

N-benzyl-1-(8-methoxyquinolin-4-yl)methanamine: 1.97 grams of 4-(bromomethyl)quinolin-8-ol was dissolved in 40 ml of dry DMF. 1.35 ml of benzylamine was added along with 4.3 ml of N-ethyl-N-isopropylpropan-2-amine. The mixture was stirred at room temperature for 4 hrs. The mixture was poured into a brine solution and extracted 3 times with ethyl acetate. The ethyl acetate solution was washed 2 times with additional brine. The ethyl acetate was dried over sodium sulfate and evaporated. The material was chromatographed on silica using methylene chloride and methanol as an eluent. Yield 1.63 grams (83%) of white solid.

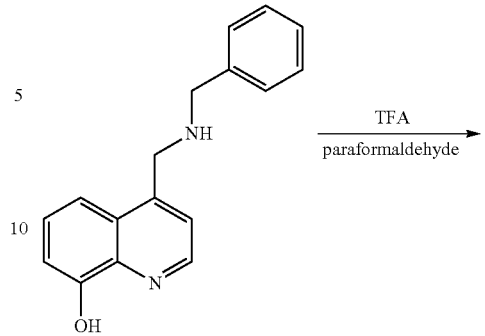

5-benzyl-5,6-dihydro-4H-benzo[de][2,6]naphthyridin-9-ol: AC110

1.63 Grams of 4-((benzylamino)methyl)quinolin-8-ol was dissolved in 40 ml of trifluoroacetic acid along with 0.22 grams of paraformaldehyde the solution was stirred at room temperature for 15 to 20 min to dissolve all of the solid. The solution was heated to 75° C. under nitrogen. The reaction was followed by HPLC. The reaction was cooled to room temperature after 20 hrs and the trifluoroacetic acid was evaporated off under vacuum. The residue was dissolved in methylene chloride and washed with a sodium bicarbonate solution. The methylene chloride was dried over sodium sulfate and evaporated to give a pale red solid. The solid was crystallized from hot cyclohexane to give 1.09 grams (64%).
$^1$H NMR (400 MHz DMSO-d6) δ 8.66 (d, 1H), 7.33 (m, 5H), 7.10 (m, 3H), 3.93 (s, 4H), 3.79 (s, 2H) m/e 277.1 (M+1).

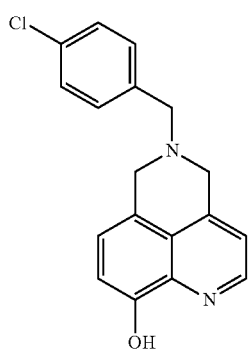

AC-117

$^1$H NMR (400 MHz, CDCl$_3$) δ 8.67 (d, 1H), 7.30 (s, 4H), 7.14-7.06 (m, 3H), 3.89 (s, 4H), 3.74 (s, 2H). MS (m/z) 311.07 (M+H)$^+$

AC-118
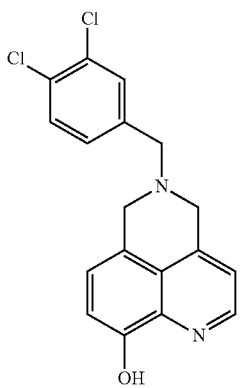
¹H NMR (400 MHz, CDCl₃) δ 8.67 (d, 1H), 7.47 (d, 1H), 7.39 (d, 1H), 7.19 (dd, 1H), 7.14-7.06 (m, 3H), 3.90 (s, 4H), 3.71 (s, 2H). MS (m/z) 345.03 (M+H)⁺
AC-119
¹H NMR (400 MHz, DMSO-d6) δ 9.66 (s, 1H), 8.71 (d, 1H), 7.53 (d, 2H), 7.31 (d, 2H), 7.28 (d, 1H), 7.14 (d, 1H), 6.97 (d, 1H), 3.87 (s, 2H), 3.81 (s, 2H), 3.73 (s, 2H). MS (m/z) 355.02 (M+H)⁺
AC-120
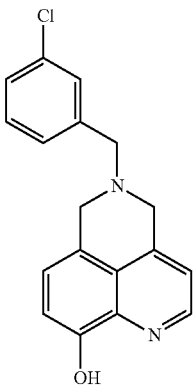
¹H NMR (400 MHz, DMSO-d6) δ 9.66 (s, 1H), 8.71 (d, 1H), 7.41-7.27 (m, 5H), 7.15 (d, 1H), 6.96 (d, 1H), 3.88 (s, 2H), 3.82 (s, 2H), 3.76 (s, 2H). MS (m/z) 311.07 (M+H)⁺
AC-121
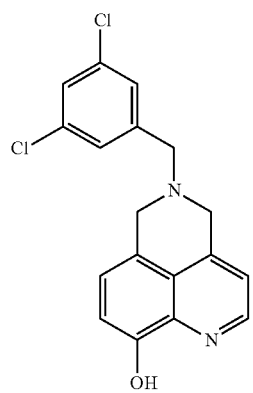
¹H NMR (400 MHz, DMSO-d₆) δ 9.67 (s, 1H), 8.72 (d, 1H), 7.52 (t, 1H), 7.40 (d, 2H), 7.30 (d, 1H), 7.16 (d, 1H), 6.97 (d, 1H), 3.90 (s, 2H), 3.83 (s, 2H), 3.77 (s, 2H). MS (m/z) 345.03 (M+H)⁺
AC-122
¹H NMR (400 MHz, DMSO-d₆) δ 9.67 (s, 1H), 8.72 (d, 1H), 7.58 (dd, 1H), 7.49 (dd, 1H), 7.36 (t, 1H), 7.30 (d, 1H), 7.16 (d, 1H), 6.97 (d, 1H), 3.96 (s, 2H), 3.90 (s, 2H), 3.88 (s, 2H). MS (m/z) 345.04 (M+H)⁺
AC-123
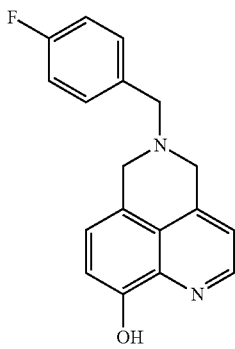
¹H NMR (400 MHz CDCl₃) δ 8.68 (d, 1H), 7.33 (dd, 2H), 7.15-7.07 (m, 3H), 7.06-6.99 (m, 2H), 3.93 (s, 4H), 3.76 (s, 2H). MS (m/z) 295.1 (M+H)⁺

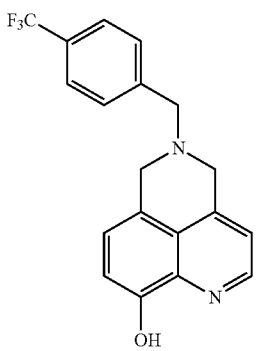

AC-124

¹H NMR (400 MHz, DMSO-d6) δ 9.66 (s, 1H), 8.72 (d, 1H), 7.70 (d, 2H), 7.58 (d, 2H), 7.29 (d, 1H), 7.15 (d, 1H), 6.97 (d, 1H), 3.90 (d, 2H), 3.85 (d, 2H), 3.84 (d, 2H). MS (m/z) 345.1 (M+H)⁺

AC-125

¹H NMR (400 MHz, DMSO-d6) δ 9.68 (s, 1H), 8.72 (d, 1H), 8.03 (d, 3H), 7.30 (d, 1H), 7.16 (d, 1H), 6.98 (d, 1H), 3.95 (d, 2H), 3.94 (d, 2H), 3.88 (d, 2H). MS (m/z) 413.08 (M+H)⁺.

The compounds described above were evaluated for the inhibition and reversal of protein aggregation as carried out using such assays as Bis-ANS Fluorescence as described in, for example, *J. Biol. Chem*, 2011, 286 (11), 9646. All compounds prepared above were measured to show EC$_{50}$ between 0.000001 to 0.10 mM in both assays in the presence of Zinc (II).

Effect of bis-ANS on Aβ1-42 Solubility and Precipitation by Zn$^{2+}$

Aβ1-42 (25 μM) in Tris-HCl buffer (50 mM, pH7.4) was incubated at RT for 10 min in the presence or absence of ZnCl$_2$ (25 μM) and bis-ANS (50 μM). Immediately following the addition of reagents, a 'time 0' aliquot was removed, diluted 25 fold in Tris-HCl buffer, and snap frozen in liquid N$_2$, then stored at −80° C. After the 10 min incubation, the mixtures were centrifuged at 154,000 g (TLA-55 rotor) for 120 min at 4° C. in an OptimaT MAX-XP Benchtop ultracentrifuge. A sample of the supernatant was then collected and compared by dot blot for peptide content to the sample of starting material to quantify how much original peptide had been lost due to precipitation.

Ionophore Studies: In general, the ionophore assay provides a measure of a molecule's ability to move metals into cells. M17 human neuroblastoma cells were plated overnight to 70% confluency (1 million cells) at the time of the experiment. All experiments were conducted in duplicate. Cells were incubated I 1 ml of Opti-MEM (Invitrogen) with added 10% FBS, Sodium Pyruvate, NEAA and PenStrep (with or without varying concentrations of compound and 10 μM of Cu$^{2+}$, Zn$^{2+}$ or Fe$^{3+}$ as chloride) for 5 hr at 37° C. At the end of the incubation, the media was removed and replaced with 1 ml PBS to dislodge the cells, which were then put into Eppendorf tubes and pelleted. The cell pellets were then used for inductively coupled plasma mass spectrometry (ICPMS) analysis of metal content as previously described in Maynard, C. J., Cappai, R., Volitakis, I., Cherny, R. A., Masters, C. L., Li, Q. X. and Bush, A. I. (2006). Gender and genetic background effects on brain metal levels in APP transgenic and normal mice: implications for Alzheimer beta amyloid pathology. *J. Inorg. Biochem.* 100, 952-962.

Dissolution of Zn-Induced Aβ Precipitates (ThT Assay): In one aspect, ThT provides a measure of large protein aggregates, such as amyloids. Aβ1-42 (10 μM) was incubated with ZnCl$_2$ (20 μM) and thioflavin (ThT) in a molar ratio of (1:2:2) for 24 hr at 37° C. on a rotating wheel in PBS (pH 6.6). Following incubation, the mixture (containing peptide aggregates) was incubated with a test compound for a further 2 hr at 37° C. with rotation. CQ and PBT2 were dissolved in DMSO to a stock concentration of 5 mM. Dilutions were made in DMSO as appropriate to 100 times the desired final concentration, then added to the reaction buffer to a final DMSO concentration of 1% v/v PBS. Untreated aggregates and DMSO controls were included with each experiment. After 2 hr incubation, samples were measure for ThT fluorescence using an LS55 (Perkin Elmer) fluorimeter. Data were generated using FL WInslab software (Perkin Elmer). Each measurement was performed in triplicate.

The foregoing examples of the related art and limitations are intended to be illustrative and not exclusive. While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

What is claimed is:

1. A compound of the formula I:

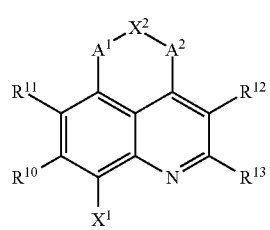

I wherein:
X$^1$ is —OH or —NR$^1$R$^2$;
X$^2$ is selected from the group consisting of —NR$^3$—, —O— and —S(O)$_{1-2}$—;

A¹ is selected from the group consisting of —C(O)— and —CH₂;

A² is selected from the group consisting of —C(O)— and —CH₂;

R¹ and R² are each independently H, substituted or unsubstituted $C_1$-$C_6$ alkyl, X—$C_1$-$C_6$ alkyl, substituted or unsubstituted $C_{5-10}$ aryl, substituted or unsubstituted —$C_{1-6}$ alkyl-$C_{6-10}$ aryl, substituted or unsubstituted $C_{1-6}$ alkylC(O)—, X—$C_{1-6}$ alkylC(O)—, substituted or unsubstituted $C_{1-6}$ alkylS(O)$_{1-2}$—, substituted or unsubstituted $C_{1-6}$alkylNR'C(O)—, X—$C_{1-6}$ alkyl-NR'C(O)—, X—$C_{1-6}$ alkoxyC(NR")— and substituted or unsubstituted $C_{1-6}$ alkoxyC(NR")—;

R' and R" are each independently selected from the group consisting of H, substituted or unsubstituted $C_{1-6}$ alkyl and substituted and unsubstituted —$C_{1-6}$ alkyl-$C_{6-10}$ aryl;

R³ is H or selected from the group consisting of substituted or unsubstituted $C_{1-6}$ alkyl, substituted or unsubstituted $C_{5-10}$ aryl, substituted or unsubstituted —$C_{1-6}$ alkyl-$C_{6-10}$ aryl, substituted or unsubstituted —$C_{1-6}$ alkyl-$C_{5-10}$ heteroaryl, substituted or unsubstituted $C_{1-6}$ alkylC(O)—, substituted or unsubstituted $C_{1-6}$ alkyl-S(O)$_{1-2}$—, substituted or unsubstituted $C_{1-6}$ alkylNHC(O)— and substituted or unsubstituted $C_{1-6}$ alkoxyC(NR')—;

R¹⁰, R¹¹ and R¹² are each independently H or substituted or unsubstituted $C_{1-6}$ alkyl;

R¹³ is H or is selected from the group consisting of X, halo, substituted or unsubstituted $C_{1-6}$ alkyl;

each X is independently selected from the group consisting of ¹³¹I, ¹²⁴I, ¹²⁵I, ³H, ¹²³I ¹⁸F, ¹⁹F, ⁷⁵Br and ⁷⁶Br;

or a pharmaceutically acceptable salt thereof.

2. The compound of claim 1, wherein X¹ is —OH.

3. The compound of claim 1, wherein X² is —NR³, wherein R³ is substituted or unsubstituted $C_{1-6}$ alkyl or a substituted or unsubstituted —$C_{1-6}$ alkyl-$C_{6-10}$ aryl.

4. The compound of claim 3, wherein R³ is $C_{1-6}$ alkyl-X, wherein X is selected from the group consisting of ¹³¹I, ¹²⁴I, ¹²⁵I, ³H ¹²³I, ¹⁸F, ¹⁹F, ⁷⁵Br and ⁷⁶Br.

5. The compound of claim 4, wherein X is ¹⁸F.

6. The compound of claim 1, wherein A¹ and A² are each independently —C(O)—.

7. The compound of claim 1, wherein R¹⁰, R¹¹, R¹² and R¹³ are hydrogen.

8. The compound of claim 1, wherein R³ is N-benzyl.

9. A compound of the formula II:

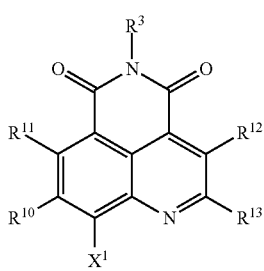

wherein:
X¹ is —OH or —NHR²;
R¹ and R² are each independently H, X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$ alkylC(O)—, substituted or unsubstituted $C_{1-6}$ alkylC(O)—, X—$C_{1-6}$ alkyl-S(O)$_{1-2}$—, substituted or unsubstituted $C_{1-6}$ alkyl-S(O)$_{1-2}$—, X—$C_{1-6}$alkylNHC(O)—, substituted or unsubstituted $C_{1-6}$ alkylNHC(O)—, X—$C_{1-6}$ alkoxyC(NH)— and substituted or unsubstituted $C_{1-6}$ alkoxyC(NH)—;

R³ is H or selected from the group consisting of X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$alkylC(O)—, substituted or unsubstituted $C_{1-6}$ alkylC(O)—, X—$C_{1-6}$alkylS(O)$_{1-2}$ substituted or unsubstituted $C_{1-6}$ alkylS(O)$_{1-2}$—, substituted or unsubstituted $C_{1-6}$ alkylNHC(O)—, X—$C_{1-6}$ alkoxyC(NH)— and substituted or unsubstituted $C_{1-6}$ alkoxyC(NH)—;

R¹⁰, R¹¹ and R¹² are each independently H, X or substituted or unsubstituted $C_{1-6}$alkyl;

R¹³ is H or is selected from the group consisting of X, halo, substituted or unsubstituted $C_{1-6}$ alkyl;

R' and R" are each independently selected from the group consisting of H, substituted or unsubstituted $C_{1-6}$ alkyl and substituted or unsubstituted —$C_{1-6}$ alkyl-$C_{6-10}$ aryl;

each X is independently selected from the group consisting of ¹³¹I, ¹²⁴I, ¹²⁵I, ³H, ¹²³I, ¹⁸F, ¹⁹F, ⁷⁵Br and ⁷⁶Br;

or a pharmaceutically acceptable salt thereof.

10. The compound of claim 9, wherein X¹ is OH and R¹⁰, R¹¹, R¹² and R¹³ are hydrogen.

11. The compound of claim 10, wherein R³ is substituted or unsubstituted —$C_{1-6}$ alkyl-$C_{6-10}$ aryl.

12. The compound of claim 9, wherein:
X¹ is —OH;
R¹⁰, R¹¹ and R¹² are hydrogen;
R³ is $C_{1-6}$ alkyl-$C_{6-10}$ aryl-X; and
R¹³ is H.

13. The compound of claim 9, wherein R³ is $C_{1-6}$ alkyl-X, wherein X is selected from the group consisting of ¹³¹I, ¹²⁴I, ¹²⁵I, ³H, ¹²³I, ¹⁸F, ¹⁹F, ⁷⁵Br and ⁷⁶Br.

14. The compound of claim 9, wherein at least one of R¹⁰, R¹¹, R¹² and R¹³ is X.

15. A compound of the formula III:

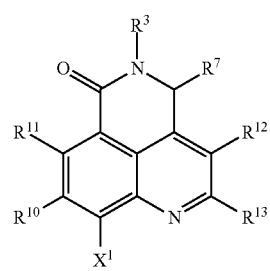

$C_{1-6}$ alkylNHC(O)— and substituted, X—$C_{1-6}$ alkoxyC(NH)—, or unsubstituted $C_{1-6}$alkoxyC(NH)—;

$R^3$ is H or selected from the group consisting of X—$C_{1-6}$ alkyl, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, X—$C_{1-6}$alkylC(O)—, substituted or unsubstituted $C_{1-6}$ alkylC(O)—, X—$C_{1-6}$alkylS(O)$_{1-2}$—, substituted or unsubstituted $C_{1-6}$ alkylS(O)$_{1-2}$—, X—$C_{1-6}$ alkylNHC(O)—, substituted or unsubstituted $C_{1-6}$ alkylNHC(O)—, X—$C_{1-6}$ alkoxyC(NH)— and substituted or unsubstituted $C_{1-6}$ alkoxyC(NH)—;

$R^7$ is H or is selected from the group consisting of substituted or unsubstituted $C_{1-6}$ alkyl, substituted or unsubstituted $C_{1-6}$ alkylC(O)—, substituted or unsubstituted $C_{1-6}$ alkoxyC(O)—, substituted or unsubstituted —$C_{1-6}$ alkyl-$C_{6-10}$ aryl and substituted or unsubstituted $C_{5-10}$ aryl;

$R^{10}$, $R^{11}$ and $R^{12}$ are each independently H, X or selected from the group consisting of substituted or unsubstituted $C_{1-6}$ alkyl and substituted or unsubstituted $C_{1-6}$ alkylC(O)—;

$R^{13}$ is H or is selected from the group consisting of X, halo, —OR', —CN, —SR', —NR'R", —NO$_2$, —CO$_2$R', —SO$_3$R', substituted or unsubstituted $C_{1-6}$ alkyl, —$C_{1-6}$ alkyl-SH, substituted or unsubstituted $C_{1-6}$ alkoxy-, substituted or unsubstituted $C_{1-6}$ alkylC(O)—, substituted or unsubstituted $C_{1-6}$ alkylC(S)—, —(CH$_2$)$_n$—NH—(CH$_2$)$_m$—NR'R", $C_{1-6}$ alkylC(NR')—, $C_{1-6}$ alkylC(NOH)—, —(CH$_2$)$_n$—C(NOH)—$C_{1-6}$ alkyl, $C_{6-10}$ aryl, —$C_{1-6}$ alkyl-$C_{6-10}$ aryl, —$C_{1-6}$ alkyl-$C_{3-10}$ heteroaryl and —$C_{3-10}$ heteroaryl;

R' and R" are each independently selected from the group consisting of H, substituted or unsubstituted $C_{1-6}$ alkyl and substituted or unsubstituted —$C_{1-6}$ alkyl-$C_{6-10}$ aryl;

each X is independently selected from the group consisting of $^{131}$I, $^{124}$I, $^{125}$I, $^3$H, $^{123}$I, $^{18}$F, $^{19}$F, $^{75}$Br and $^{76}$Br;

m and n are each independently 1, 2 or 3; or a pharmaceutically acceptable salt thereof;

provided that when $R^7$ is phenyl and $X^1$ is —OH, then $R^3$ is not benzyl.

16. The compound of claim 15, wherein $X^1$ is OH and $R^{10}$, $R^{11}$, $R^{12}$ and $R^{13}$ are hydrogen.

17. The compound of claim 15, wherein $R^3$ is $C_{1-6}$ alkyl-$C_{6-10}$ aryl.

18. The compound of any claim 15, wherein:

$X^1$ is —OH;

$R^{10}$, $R^{11}$ and $R^{12}$ are hydrogen;

$R^3$ is —$C_{1-6}$ alkyl-$C_{6-10}$ aryl; and $R^{13}$ is H or substituted or unsubstituted $C_{1-6}$ alkyl.

19. The compound of claim 15, wherein at least one of $R^{10}$, $R^{11}$, $R^{12}$ and $R^{13}$ is X.

20. A pharmaceutical composition comprising a therapeutically effective amount of a compound of any one of claim 1, 9 or 15, and a pharmaceutically acceptable excipient.

* * * * *